(12) United States Patent  
Solomon

(10) Patent No.: US 8,123,720 B2  
(45) Date of Patent: Feb. 28, 2012

(54) INTELLIGENT MEDICAL DEVICE SYSTEM DYNAMICS FOR BIOLOGICAL NETWORK REGULATION

(76) Inventor: Neal Solomon, Oakland, CA (US)

( * ) Notice: Subject to any disclaimer, the term of this patent is extended or adjusted under 35 U.S.C. 154(b) by 219 days.

(21) Appl. No.: 12/462,783

(22) Filed: Aug. 7, 2009

(65) Prior Publication Data

US 2010/0069832 A1 Mar. 18, 2010

Related U.S. Application Data

(60) Provisional application No. 61/188,369, filed on Aug. 8, 2008.

(51) Int. Cl.  
*A61M 31/00* (2006.01)

(52) U.S. Cl. .................................... 604/93.01

(58) Field of Classification Search ............... 604/890.1, 604/891.1, 65, 66, 93.01, 19, 20; 600/300; 706/13  
See application file for complete search history.

(56) References Cited

U.S. PATENT DOCUMENTS 6,567,703 B1 * 5/2003 Thompson et al. ............. 607/60  
2005/0096587 A1 * 5/2005 Santini et al. .................. 604/66  
* cited by examiner

*Primary Examiner* — Christopher D Koharski

(57) ABSTRACT

The intelligent medical device (iMD) system coordinates the dynamics of hardware and software components in a self-organizing autonomous system. The iMD system uses advanced modeling and metaheuristics to solve complex optimization problems involving the customization of medical therapies. The system uses evolvable hardware and reprogrammable features to coordinate the diagnostic and therapeutic functions of the iMDs.

20 Claims, 32 Drawing Sheets

FIG. 1

Hybrid Control System for Integrated iMD System

System Layers:

1 Device module
2 Specialized device
3 Multi-functional device

4 Multiple devices
5 Main devices & satellites
6 Node to node devices
7 Internal & external devices Logic
8 Chip(s) (hardware)
9 Modeling Software
10 Multi-agent system (MAS)
11 Hybrid metaheuristics for solving MOOPs
12 Autonomous software system for network regulation
13 Regulatory network system organization

FIG. 21
Phase I
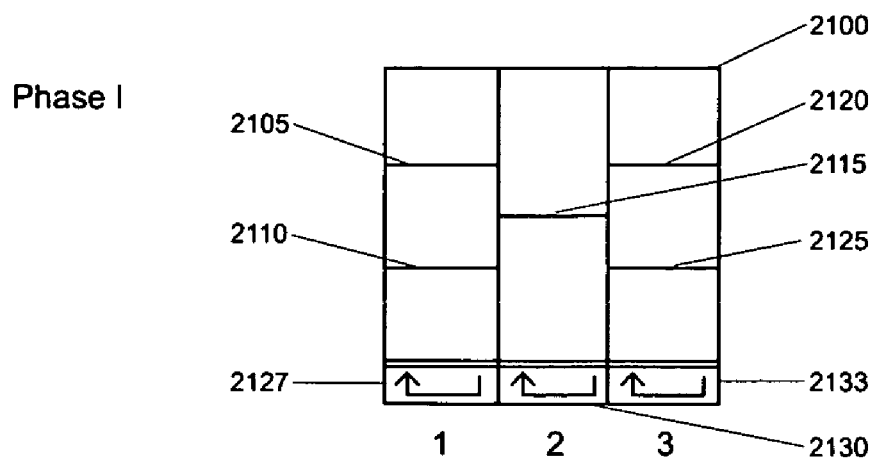
Phase II
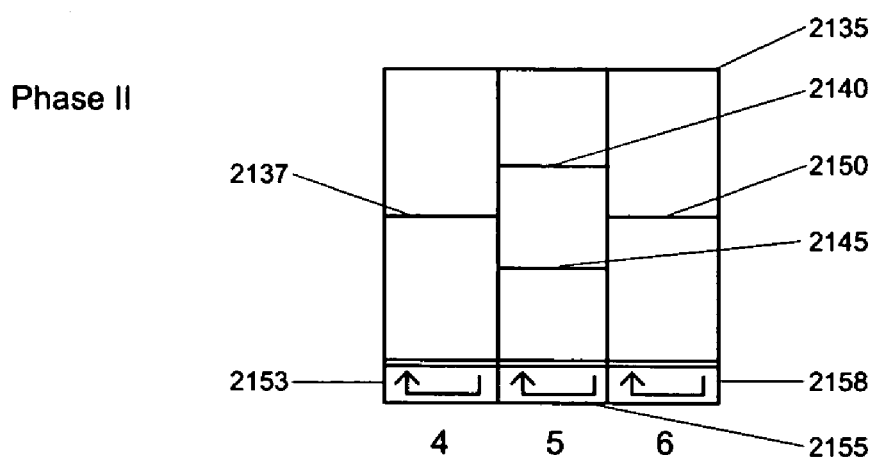
Phase III
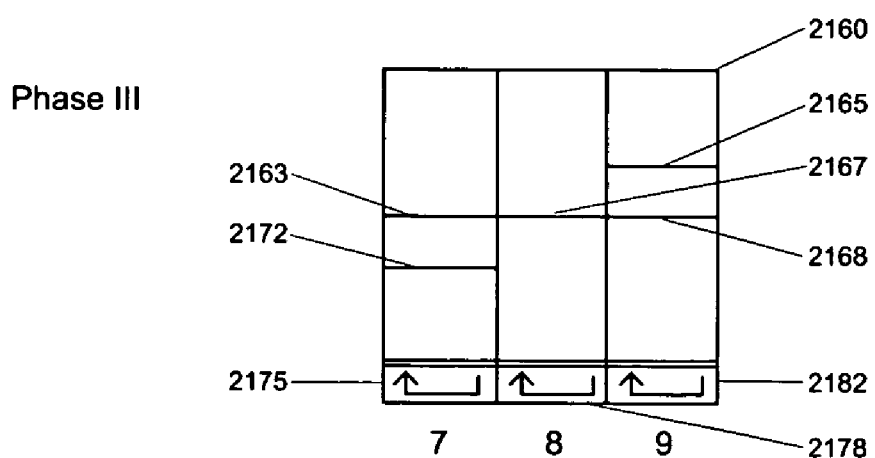

FIG. 30

| | Data collection | Diagnosis and problem solving | Therapy |
|---|---|---|---|
| Hybrid Metaheuristics | | | |
| Neuro | AIS & SS / TS | AIS & AMP - MOOP | AIS |
| Cardio | ACO & EGA | ACO & SS - MOOP | ACO & AMP |
| Cancer | SS / TS & EGA | AIS & EGA - MOOP | AIS & ACO |
| Immune | PSO & SS | SDS & EGA - eMOOP | AIS & PSO |
| Endocrine | ACO & EGA | AIS & PSO - eMOOP | PSO & EGA |

3000                    3010                    3020

| | |
|---|---|
| Local Search - | scatter search (SS), tabu search (TS), adaptive memory programming (AMP) |
| EGA - | efficient genetic algorithms (EGA) |
| Swarm Intelligence - | art colony optimization (ACO), particle swarm optimization (PSO), stochastic diffusion search (SDS) |
| Artificial Immune system - | artificial immune system (AIS) |
| Optimization problems - | bi-objective optimization problem (BOOP), multi-objective optimization problem (MOOP), evolving multi-objective optimization problems (eMOOPs) |

INTELLIGENT MEDICAL DEVICE SYSTEM DYNAMICS FOR BIOLOGICAL NETWORK REGULATION

CROSS-REFERENCES TO RELATED APPLICATIONS

The present application claims the benefit of priority under 35 U.S.C. §119 from U.S. Provisional Patent Application Ser. No. 61/188,369, filed on Aug. 8, 2008, the disclosure of which is hereby incorporated by reference in their entirety for all purposes.

FIELD OF THE INVENTION

The invention involves the dynamic operation of medical devices and components. The invention applies to diagnostic and therapeutic aspects of medical intervention. The medical device system involves the coordination of hardware and software components by using modeling processes. The system applies advanced metaheuristics to solve complex medical device problems. The system also uses evolvable hardware components in medical devices.

BACKGROUND

As scientists discover the mechanics of genetic processes, our understanding of the sources of diseases increases. The benefits of understanding genetic dynamics and proteomics regulatory processes assists in development of a new generation of medical devices able to diagnose, regulate, manage and cure complex diseases. The potential exists to develop personalized drug therapies to target specific genetic pathologies.

Regarding diagnostic systems, MEMS is an umbrella for a class of new medical devices able to identify genetic mutations and proteomic dysfunctions. While largely external in vitro devices, DNA microarrays, RNA microarrays and protein microarrays provide feedback to identify an individual's genetic information. Protein microarrays use antibodies to assess protein functional responses. In addition, whole cell assays test cells with analytes to assess specific responses to chemical inputs. Multi-phenotype cellular arrays are used for bio-sensing of specific inputs in order to study cell functions.

Though DNA, RNA, protein and whole cell arrays have developed separately, a new generation of lab on chip (LOC) and micro-total analysis systems (µTAS) technologies have emerged as well that integrate several functions in a single device. These multi-purpose arrays provide clinical diagnostic data to practitioners.

In addition to these external devices, the evolution of radiological diagnostic tools has provided a revolution to analytical practitioners. In particular, the use of CT, PET and MRI technologies provides detailed data on specific disease progression. In addition to these external radiological diagnostic technologies, the internal sensing "pill" camera records and transmits digital images to substitute for the surgical intervention of exploratory surgery. Finally, the use of implanted sensors assists in the regulation of simple deterministic expert systems.

The convergence of nanotechnology with biology has produced "bionano" devices. In the main, the use of nanotechnology is limited to particles that are targeted to specific tissues in order to identify pathology and, when combined with directed radiation, provide a therapeutic alternative. The advent of self-assembled peptide nano-biomaterials provides interesting opportunities for diagnostics and therapeutics. The use of nano-scale devices, in which collective behaviors are controlled for therapeutic as well as diagnostic modes, provides an advancement of the bionano field.

Regarding therapeutic medical devices and systems, the field has evolved from the development of the hearing aid and the cardiac pace maker. For instance, the implantable brain pacemaker has been developed to regulate epileptic energy pulses and blood glucose monitoring is regulated with an insulin pump. Moreover, implantable pain management devices are used to control chronic pain. Microfluidic devices to target drug delivery, primarily using a deterministic expert system control model, have also been developed. All of these devices are simple single-function mechanisms targeted to a specific disease or disorder.

An emerging scientific field is providing a new set of technologies from bio-inspired computing. Complexity science deals with self-organizing systems that learn in indeterministic environments. The inspiration from the autonomic nervous system and the human immune system provide computing systems that emulate these complex biological processes. Autonomic computing self-diagnoses, self-heals and self-regulates distributed networks. The human immune system provides inspiration for immunocomputing models that emulate protein regulatory network behaviors in order to solve complex optimization problems. Swarm intelligence metaheuristics provides solutions to optimization problems as well. For instance, the ant colony optimization (ACO) metaheuristic provides a model to solve network computing problems. These models share the ability to develop solutions to problems in self-organizing systems, including plasticity behaviors, in indeterministic environments. In effect, these complex computing and control systems learn. So far, these complex computing models have not been applied to medical devices.

The ability to use genetic and proteomic information to solve complex pathologies provides a new generation of opportunities to build medical devices that are customized to each individual's specific disease(s). Our understanding of cancer, for instance, as the combination of multiple genetic mutations, suggests that each disease type is classed into a typology that can be solved with specific targeted therapies. Given this new knowledge, it is logical to build medical devices that are personalized to specific diseases of each individual. In particular, the use of medical devices focused on solving problems involving pathologies associated with cardiovascular, neurological, immunological and endocrinological systems, and with cancer, is a next step.

Each of the prior medical devices has limitations. For the most part, none of the implantable medical devices are "intelligent". Rather, they are simple deterministic systems. They are also single function devices focused on a specific narrow medical problem. Because they are merely deterministic expert systems, they do not combine diagnostic and therapeutic functionality. In the diagnostic mode, they do not provide sophisticated modeling functions. Further, prior MDs are not networked since they typically involve a single device performing a single function. Finally, these devices are not useful in personalized medicine, which require complex analysis and targeting of individual therapies to unique problem sets.

What is needed? We need active intelligent medical devices that are able to work with other medical devices to solve multiple medical problems. We need complex medical devices that are capable of integrating diagnostics and therapeutics in order to maximize efficiency, to promote early detection and treatment and to modify functionality with feedback mechanisms to solve complex biological optimization problems in biological regulatory networks. The present system develops an intelligent multifunctional medical device system.

Problems That The System Solves

The present system solves a range of problems. How can we develop an intelligent medical device (iMD) that coordinates diagnosis and therapy? How can the iMD coordinate sensors and integrated circuits? How is the processing of chemical and biological fluids administered by using the iMD? How is the implantable iMD coordinated with external computation and modeling? How does the device collect samples and data in real time? How does one integrate multi-functionality into an efficient iMD design? How is the implantable device installed with minimal invasiveness? How are nano-components integrated into the iMD? How does the iMD use sensors and probes for maximum effect? How does the iMD efficiently analyze biological data? How are solutions to complex problems developed and refined in the iMD? How is drug delivery optimized in the iMD? How can we construct customized drugs for therapies to individual patient pathologies? How can an iMD self-organize and adapt to indeterministic environmental conditions? How can multiple iMDs be coordinated, particularly for multiple applications? Solving these problems presents opportunities to develop a new generation of highly effective medical devices.

SUMMARY OF THE INVENTION

The iMD system is coordinated by a hybrid control system that self-organizes hardware and software components. The hardware system is composed of interdependent integrated diagnostic and therapeutic modules that analyze and solve medical problems associated with complex diseases. Multiple reprogrammable integrated circuits and a system on a chip (SOC) manage the computing functions of the iMD system.

The software system uses a multi-agent system (MAS) to coordinate the behaviors of collectives of intelligent software agents to automate the controls of the functional modules. The MAS administers the modeling components to solve multi-objective optimization problems (MOOPs) and to provide therapeutic solution options. The system uses EDA software to organize the hardware components. Advanced metaheuristics provide algorithms to solve MOOPS.

The system reconfigures its hardware architecture in order to optimize its functionality to solve MOOPs in real time. The reprogrammable characteristics of the iMD constitute a class of evolvable hardware.
Novelties An iMD is a micro-robotic device that resembles a miniature Mars landing craft because of the requirement to remotely collect data, analyze the data and provide external therapeutic functionality. Because of this insight, robotics is a useful comparison of the iMD's components, particularly since the devices reconfigure their internal apparatus in response to external stimulus. Specifically, iMDs are a special class of evolvable hardware (EHW). EHW has been applied to FPGAs and to collectives of robotics, but not to iMDs.

The application of advanced metaheuristics to iMDs shows the ability to solve multi-objective optimization problems (MOOPs). By computationally modeling complex problems, optimization solutions are provided by iMDs in real time. Further, modeling allows the system to anticipate pathology developmental scenarios that are more easily solved.

iMDs are smart adaptive systems that are modular, flexible, integrated and customized.

ADVANTAGES OF THE INVENTION

The invention allows the integration of diagnostics with therapeutics in a medical device, thereby increasing the efficiency of the therapeutic modality. The integrated device allows the tracking of therapies by assessing feedback processes in order to more effectively manage complex regulatory networks.

The invention facilitates automated and rapid prototyping of therapies to complex medical pathologies. The invention employs reprogrammable components, particularly reconfigurable components in the therapeutic module, to accomplish customized personalized medicine for evolving diseases.

The co-evolution of semiconductor and microfluidic components in an automated medical device facilitates rapid solution generation and application to optimization problems involving complex diseases.

DESCRIPTION OF THE INVENTION (1) Hybrid Control System for Integrated iMD System The hybrid control system for the integrated iMD system consists of thirteen layers. On the first layer is a single iMD device module. On the second layer is a specialized iMD. On the third layer is a multifunctional iMD.

Multiple devices are on the fourth layer. The fifth layer contains the main device and satellite devices, while the sixth layer consists of a configuration of node-to-node devices. On the seventh layer of the system are internal and external devices.

The logic of the system is organized on the eighth and ninth layers, with semiconductor hardware on the eight layer and modeling analysis on the ninth layer. The software system is on the tenth layer, featuring a multi agent system (MAS). Hybrid metaheuristics are used for solving MOOPs at the eleventh layer. The autonomic computing system for network regulation is at the twelfth layer and the regulatory network organization for system plasticity occurs at the thirteenth layer.

Overall, this model presents the flexibility of an integrated iMD system for interaction and learning in indeterministic environments.
(I) Solving Optimization Problems
(2) System for the Combination of Device Processes to Solve MOOPs One of the challenges of the iMD system is how to solve complex optimization problems involving diagnostics and therapeutics. Each disease has a unique combination of genetic mutations that manifests as pathology. Analyzing patient data to discover the parameters of the genetic mutations presents a combinatorial optimization problem. Each disease has a set of information constraints that sets the parameters for classification of multi-objective optimization problems (MOOPs). The main diagnostic challenge is to delimit the parameters of pathology MOOPs which underlie genetic disease.

In order to identify the MOOPs, a combination of device processes is employed. These include the multiple analytical functions of iMDs, external computer resources, software systems and networking systems. The main software functions involve modeling and problem solving algorithms. In effect, the challenge is how to solve a complex puzzle in which the data sets are incomplete. The algorithms are required to build models to identify the trade-offs of MOOPs in order to zero in on a combinatorial optimization problem. One problem is to find ways to sort through a range of gene combinations in order to identify the specific regulator genes. To do so requires the operational modeling of protein regulatory networks and the subtraction of specific proteins and their source genes. Even a single dysfunctional peptide within a mutant protein may cause a different effect than another peptide in the same protein, thereby illustrating the complexity of identifying gene combinations that are traced to diseases.

While identification of the MOOPs of genetic disorders is critical, identification of the solutions to the MOOPs is even more essential if we are to discover drugs or procedures to cure or manage diseases. Though the iMD system continually builds and refines diagnostic models to clarify MOOPs, the modeling process is guided to development of therapeutic solutions. The key to development of multi-objective optimization solutions (MOOSs) is the narrowing of the range of solution options. Each solution, then, is presented within a narrow range of solution constraints. In effect, each MOOS is a custom solution to a complex optimization problem.

Once the solution options are generated by the modeling system in the analytical module, the therapeutic module applies the solutions by developing customized drugs or a combination of drugs and procedures. In some cases, a drug is applied to solve a particular problem in a patient only after the confirmation of the existence of, or the specificity about the condition of, a particular set of genes.

(II) Software System
(3) Multi-agent System Using Software Agents Integrated into iMD Network Each iMD has a complex software system that connects the elements. Since the iMD consists of several different modules—analytical, diagnostic, therapeutic, storage, data collection, etc.—each device is organized like a modular component in a network. Each device has software that enables its diagnostic and therapeutic processes as well as the regulatory functions involving operational mechanics. Because the software system operates in a network, it uses simultaneous parallel processes to organize the multiple components.

The software system is modular. As the software system encounters new challenges, it adapts to the biological system feedback by generating new code and combining a new set of algorithms to solve MOOPs. The system uses genetic programming elements to solve novel problems. This evolutionary component of the iMD system provides a learning process that allows the software system to expand beyond its original programming limits.

In order to promote adaptive operations, the software system proceeds on two fronts. First, it requests assistance for problem solving from external computation resources, which (wirelessly) update program code with new algorithms. Second, the system employs a multi-agent system, which autonomously solves problems on demand.

The iMD software system links multiple devices into a network. Each device module operates independently, while also working with other modules in the same device as well as the overall iMD network. This coordination of the multiple device components is organized by the multi-agent software system (MAS).

Software agents are autonomous program code that operates in the MAS. The intelligent mobile software agents have specific tasks to achieve by representing specific elements of the iMD. For instance, specialist software agents are focused on solving problems associated with pathology modeling within the analytical module from data in the diagnostic module, while others are tasked with the regulatory operations of the diagnostic and therapeutic modules.

Software agents are either cooperative or competitive. While most agents are cooperative, they work together in a division of labor by sharing the specialized capacities of the different agents within each module that focus on a specific task. On the other hand, competitive agents, typically structured in teams, are used for problem solving within time constraints. Competitive agents use game theoretic modeling and incentives to create teams that compete to achieve a goal. For instance, competitive agents are used to launch a set of probes to achieve a task, with the first probe to produce demonstrable diagnostics constituting the winning software agent team.

Software agents are useful in the iMD system for the data collection, analysis and modeling components of the diagnostic module and for the drug combination, drug synthesis, drug delivery and refinement elements of the therapeutic module. Because of the modular architecture of the iMD, multiple IMSA functions are processed simultaneously by the SoC.

Since each iMD module contains an integrated circuit for controlling functionality, the utility of software agents occurs by the agents interacting with the main operating system of each module. However, the agents cross over and interact with program code of other modules in order to perform tasks by sending and receiving requests for active functions and by solving problems. In this way, agents "represent" a specific module and move from one module to another to achieve a task. With the whole system interoperating with multiple software agents, this network of actions produces a complex intelligent system.

The iMD MAS is made the more complex in the context of the overall iMD system network. Multiple devices contain multiple modules, each with multiple software agents. The agents are able to move from device to device in order to solve complex problems. This integrated networked MAS is critical in order for the system to manage complex behaviors.

(4) Method for Network Regulation of iMD System

Autonomic computing presents a model for operating the iMD network computing systems. Autonomic computing provides self-management tools by self-configuring, self-regulating, self-correcting, self-defending and self-optimizing distributed computer networks using Software agents. The present system uses Software agents for autonomic behaviors of self-regulation and self-optimization to organize and reorganize modules in the iMD network to perform specific diagnostic and therapeutic functions.

Software agents use autonomic computing behaviors to perform the regulatory functions of scheduling and planning tasks by continually updating the priorities of schedules. The software agents use efficient genetic algorithms and hybrid metaheuristics to continually reorganize network priorities to meet goals.

The system uses game theoretical modeling to structure the software agent collectives to perform specific analytical and functional behaviors. In an analogy, the system operates in ways similar to a group of chefs in a kitchen, constantly coordinating multiple tasks to achieve the common goals of feeding disparate customers within time constraints. For the iMD system, the software agents work together to perform specific functions with the aim to fulfill specific tasks.

Though the autonomic computing system operates at the level of regulatory housekeeping to organize operational functions, application of the autonomic computing principles to the iMD system provides intelligent and autonomous aspects to the operating system.

(III) Evolvable Hardware
(5) System for Evolvable Hardware in iMDs Using Convertible iMDs for Custom Multi-functionality Evolvable hardware (EHW) reconfigures the position of an extensible system. An example of EHW is a field programmable gate array which restructures its architecture from one ASIC position to another ASIC position in order to accomplish multiple system functions. Each iMD uses the EHW reconfiguration architecture to reorganize the geometry of its spatial structure. The internal mechanisms of each functional module modify their geometric architecture in order to optimize their operational effectiveness by continually modifying the configuration of their integrated "circuitry" and by changing the structure of the partitions and chambers of their internal microfluidic circuitry. The reconfiguration of the chip circuitry of the iMD's FPGAs or SoCs co-adapt to the changing architectural modes of the physical hardware components.

The iMD module hardware components are organized in compartments contained by partitions. Since the partitions are movable, the compartments are able to change their structural configurations. As an analogy, the periodic reshaping of the partitions in an office provides a model for the iMD. The complex network of microfluidic tubing that is integrated into the iMD modules occurs in the "flooring" and "siding" of each module layer. Each module is able to transform the structure of each component or layer independently. This is similar to configuring a floor of an office building on demand in preparation for a new tenant.

The ability to reconfigure the geometries of specific layers on demand within each module allows the system to organize functional processes for different operational problems. The structural transformation capability of the lab on a chip (LOC) component allows substantial flexibility in designing experiments to maximize efficiency of diagnostic and analytical processes. Further, the ability to restructure the composition of module layers or components on demand allows the iMD to flexibly synthesize different chemical elements and biological processes. While each module permits only one or two layers to restructure at any time, primarily in order to preserve functional utility of the existing operational layers, the transformation process of integrating EHW into the iMD system allows efficiency as well as flexibility in performing complex diagnostic and therapeutic functions.

The combination of multiple reconfigurations of layer architectures within iMD modules allows each iMD to perform switching from particular specialized functions. The EHW application to iMDs allows the iMDs to solve multiple complex problems over a sequence of phases.

(6) Method for Coordination and Synchronization of Reprogrammable iMD

The advantage of using EHW in iMDs is to reconfigure the structure of the module layers as the environment changes, thereby allowing a new set of tools to solve the new problems. The main way to restructure the iMD hardware is to synchronize the restructuring with reconfigurable computing components of FPGAs and SoCs. The FPGA (or other complex programmable logic device) is the engine that drives the reconfiguration of each iMD module from one architecture configuration to another. This connection between the reconfigurable chip and the reconfigurable iMD is particularly useful in indeterministic environments which require the iMD to autonomously restructure in order to solve MOOPs. In this way, the transformational iMD integrates structure and function.

As the FPGA receives sensor data, from biological system interaction and from biological sample analysis and experimentation, it models the data and solves MOOPs that require the iMD to change architectural configuration. The iMD then engages in the process of structural transformation and performs a function to solve a MOOP by interacting with the environment. In indeterministic environments, the FPGA is also indeterministic, that is, not pre-programmed with specific control management software. The iMD is therefore programmed to continuously respond to a changing environment. The complex optimization problems presented by indeterministic environments are evolutionary MOOPs (eMOOPs), which require the co-adaptation of the FPGA and the transformational iMD.

Each iMD is a sort of network, with multiple functional modules. The embedded SoC that controls the overall iMD functions continuously and reorganizes the transformation mechanisms of each module layer. The FPGA on each layer controls the specific module transformation sequence and operational control process.

The system also integrates into a multiple iMD network as an additional dimension of coordinated reconfiguration.

Though not all iMD module layers are transformational, the ability to integrate EHW functionality into iMDs advances the utility of the present system by a generation.

(IV) Modeling
(7) Method for On-demand EDA Modeling for Transforming Geometries of iMD Electronic design automation (EDA) is a form of computer aided design (CAD) software which lays down the routing architecture for integrated circuits. EDA software is also useful for the design of iMD modules. 3D EDA software is used to organize the architecture for multiple layers of 3D chips and is applicable to designing the layers of the iMD modules.

EDA is used to model both the architectural pathway vectors of FPGAs and SoCs and the iMD module layers. Software agents organize the on-board EDA modeling processes to optimize the configurations of the chips and the internal iMD "circuitry." The EDA system itself solves MOOPs within constraints in order to develop best case scenarios for the restructuring of channel geometries of biochips. The EDA system models the layers and the vias of the micro-channels of the internal device "plumbing" system.

The EDA system is triggered by the FPGAs as their program code is activated by a set of threshold events motivated by either internal programming criteria or external environmental change. The EDA analysis is modeled by the FPGA of each layer and the SoC of each iMD. However, the software agents oversee the reconstruction of each transforming layer by interacting with actuators and sensors on each layer and reporting back to the FPGA or SoC for new instructions. EDA modeling is also performed by external computer resources, particularly for iMD network component architecture transformation coordination.

(8) Method for EDA Modeling for Parallel Architecture Transformation of Multiple Devices in iMD Network Taken to the next level, the ability to change the structure of specific modules in the overall iMD network on-demand in order to adapt to the needs of a changing environment presents an evolutionary system. When one part of the system requires a new solution while the system is solving one problem, another iMD transforms its architecture and proceeds to solve the problem. The system presents the mechanisms for parallel architecture transformation of multiple devices in the iMD network to solve simultaneous problems.

The iMD system is designed to solve MOOPs by periodically restructuring its hardware configurations. By coordinating multiple iMD behaviors, the system integrates routing architecture changes by using EDA modeling with the scheduling functions of the software agents.

In a further extension of the EHW model to network iMD components, the EDA modeling system develops anticipatory processes. This is performed by developing complex models to solve eMOOPs and presenting multiple scenarios within a range of probabilities. As the environment changes in unpredictable ways, the modeling scenarios track the biological system performance and make predictions of the evolutionary pathway vectors. The EDA system then projects evolutionary architecture structural transformations of specific iMD module layers to prepare for imminent probable MOOP solutions.

Given the transformational functionalities, the dynamics of the iMD network are extremely complex, particularly with multiple simultaneous pathology problem solving.

(V) Metaheuristics (9) System for Hybrid Metaheuristics Using iMDs for Specialized Applications A computational metaheuristic is a logical process used in computational systems in which optimization problems are solved by employing a memory component for learning. Several main classes of metaheuristics include local search, swarm intelligence, immunocomputing and genetic algorithms, with sub-classes of each category used to solve a different type of optimization problem. Hybrid metaheuristics are applied to the iMD to solve complex biomedical optimization problems. The application of metaheuristics to the iMD system provides a learning mechanism and artificial intelligence to autonomously solve novel problems in real time. The iMD system uses multiple hybrid metaheuristics to solve problems simultaneously.

Local search metaheuristics, developed by Glover, consist of scatter search (SS), tabu search (TS) and adaptive memory programming (AMP) computational techniques to store in memory the previously searched domain. For example, in the search and rescue process of finding a lost hiker, searchers check off the areas previously searched in order to devote limited resources to the areas not yet searched. SS uses a positive model for searching the forward unexplored search space, while TS uses a negative model for excluding the previously search space and AMP continually updates its memory to efficiently guide the future search process. Local search metaheuristics are used to solve bi-objective optimization problems (BOOPs) and simple MOOPs.

Genetic algorithms, developed by Holland, emulate the genetic process by breeding populations of algorithms to solve BOOPs and simple MOOPs. GAs create random mutations to generate new populations and test the results against the problem at each phase of development. While there is no memory as such, GAs successively create their own learning process as new generations are bred and matched to the environmental problem.

New types of GAs manipulate assumptions such as the mutation pathway vectors to create focused, and efficient, GA models within time constraints. Also, hybrid GAs solve particular classes of problems. GAs combined with scatter search, for example focuses the population generation vector.

Swarm intelligence, borrowing from bio-inspired systems, consists of ant colony optimization (ACO), particle swarm optimization (PSO) and stochastic diffusion search (SDS). ACO emulates the behavior of ants by creating a memory system that mimics ant pheromones, storage and access mechanisms. PSO emulates the behavior of bees by registering the nearest neighbor interactions in real time. SDS uses a similar system of swarm behaviors, but accesses the behavior of any member of the swarm rather than only the nearest neighbor. All of these metaheuristics are used to solve complex MOOPs.

Artificial immune systems (AISs) emulate the human immune system operation in which the humoral immune subsystem stimulates a cascade antibody process to fight off an antigen and in which the adaptive immune subsystem solves novel antigen problems and passes the solution to the humoral system for activation when the same antigen is discovered. AISs are used to solve complex eMOOPs in which the problem is constantly changing, for instance in changing environments.

All of these metaheuristics have a place in the iMD system. The local search models are applied to a narrow initial diagnostic problem by seeking to delimit the parameters. GA is applied to BOOPs to solve diagnostic and therapeutic problems within computational constraints. Swarm intelligence metaheuristics are used in network coordination problems to organize the interoperations between the MOOPs within and among iMDs. Finally, the AIS metaheuristic is used to solve eMOOPs that involve diagnostic-therapeutic interactive problems. Each metaheuristic is tailored to a specific class of optimization problem that efficiently matches the technique to the solution generation process within constraints.

The hybridization of the metaheuristics techniques provides a novel approach to solve complex optimization problems in real time. In these schemata, the local search methods are combined with GAs, for example. The GAs or the local search methods are combined with the swarm intelligence and AIS methods as well. These unique hybrid metaheuristic combinations are applied to various classes of optimization problems in the iMD system on demand.

Software agents are used to request and guide the metaheuristic techniques as problems emerge and the modeling analyses require solution options.

(10) System for Parallel Distributed Network Computing Co-evolving with Device and Network Multifunction Interoperability While metaheuristics computational methods are applied to solve specific diagnostic and therapeutic iMD optimization problems, the existence of complex multifunctional behaviors in the iMD network system suggests the need to organize multiple simultaneous processes. In the present system, hybrid metaheuristics are generated and recombined on demand to solve a new set of optimization problems in different modules of the iMD network.

The iMD system uses hybrid metaheuristics to solve problems involving pathology detection, data collection, diagnosis, sensor network control, scheduling, module architecture restructuring, integrated circuit reprogramming and reconfiguration, custom drug therapy design, drug delivery and refinement, pathology tracking and drug modulation. Further, because the system integrates multiple iMDs into a distributed network, these multiple functions are cooperative and simultaneous, operating in parallel. The hybrid metaheuristics are combined and recombined on demand to solve critical problems throughout the network. As the iMDs attack multiple pathologies, the system combines the various metaheuristics to facilitate the process in a parallel distributed network configuration. The system manifests the multifunctional dynamics of the parallel use of hybrid metaheuristics techniques to solve the various complex optimization problems simultaneously.

(11) Immunocomputing Metaheuristic Applied to Solve eMOOPs in Networks of iMDs

Immunocomputing is one the most complex metaheuristics techniques since it emulates one of the most complex and effective biological systems. Because artificial immune systems (AISs) emulate the adaptive immune system, they are designed to solve particularly hard evolutionary problems which require novel solutions. As the biological environment of the iMD constantly changes, the system uses AISs as a last line of defense to solve eMOOPs. Hybrid AISs are used in the iMD system, which combine local search, GA and swarm intelligence techniques to fortify the different levels of the AIS problem solving process.

Hybrid AIS techniques are employed to solve iMD network eMOOPs. The interactions between the multiple functional modules of network iMDs require creating novel solutions to evolving MOOPs in the biological system. Specifically, the parallel solution generation of multiple diagnostic and therapeutic problems involves the application of AISs. While one layer of the AIS is solving diagnostic problems another layer of the AIS is simultaneously solving therapeutic regulatory problems. This process is possible because of the use of modeling to anticipate the progress of the evolutionary MOOPs which derives from an indeterminate environment.

(12) Method for Algorithm Switching in iMD System

Since the iMD system uses multiple metaheuristics in order to solve problems, and since the system is constantly solving multiple problems simultaneously in the distributed network by employing different modules in multiple iMDs, the present system provides for the switching between algorithms. Software agents are used to control and manage the metaheuristic system in the iMD network. The software agents initially cooperate to achieve common goals within specific iMD modules. However, the software agents break into competitive teams to represent specific module tasks on demand. This competitive model uses computer modeling resources from specific modules to craft specific hybrid metaheuristic algorithms on demand which create customized computational algorithms for use in solving optimization problems.

The use of metaheuristics in the iMD system is aimed at progressive learning in indeterminate environments to solve critical problems. The use of algorithm switching is intended to sort the priorities of the iMDs and to move the resources from one location to another as the system requires in order to most efficiently maximize the utility of the overall network. With algorithm switching protocols, the overall iMD system is able to constantly transform its structure to solve problems. As diseases evolve, the iMD network co-evolves by restructuring its geometrical architecture and reprogramming its computation resources to provide diagnostic and therapeutic plasticity behaviors to solve the problems. The iMD continuously prioritizes and reprioritizes a schedule of operation to efficiently allocate iMD component functions using dynamic traveling salesman algorithms.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DESCRIPTION OF THE DRAWINGS

FIG. 1 is a table listing system layers.

FIG. 21 is a set of drawings showing FPGAs on each layer of the therapeutic module in an iMD restructuring each layer and the FPGAs in sequence.

FIG. 30 is a table of hybrid metaheuristics applied to neurological, cardiological, cancer, immunological and endocrinological systems.

DETAILED DESCRIPTION OF THE DRAWINGS

The intelligent medical device system is a complex network of devices that perform customized diagnostic and therapeutic medical functions. The iMD system can be configured in different ways to accommodate problem solving for multiple medical pathologies. The iMD system is controlled by semiconductors and software systems. The chips consist of a system on a chip (SoC) component that is operable with a multi-agent software system. When the system connects multiple individual iMD devices and other devices, such as satellites and computer resources, the system has network capabilities. In general, a complex configuration of the iMD system is capable of addressing two or more pathologies simultaneously, which gives it flexibility.

The iMD system consists of several system layers. FIG. 1 shows the hybrid control system for the integrated iMD system, consisting of thirteen layers. On the first layer is a single iMD device module. On the second layer is a specialized iMD. On the third layer is a multifunctional iMD.

Multiple devices are on the fourth layer. The fifth layer contains the main device and satellite devices, while the sixth layer consists of a configuration of node-to-node devices. On the seventh layer of the system are internal and external devices.

The logic of the system is organized on the eighth and ninth layers, with semiconductor hardware on the eight layer and modeling analysis on the ninth layer. The software system is on the tenth layer, featuring a multi agent system (MAS). Hybrid metaheuristics are used for solving MOOPs at the eleventh layer. The autonomic computing system for network regulation is at the twelfth layer and the regulatory network organization for system plasticity occurs at the thirteenth layer.

Figure 2:
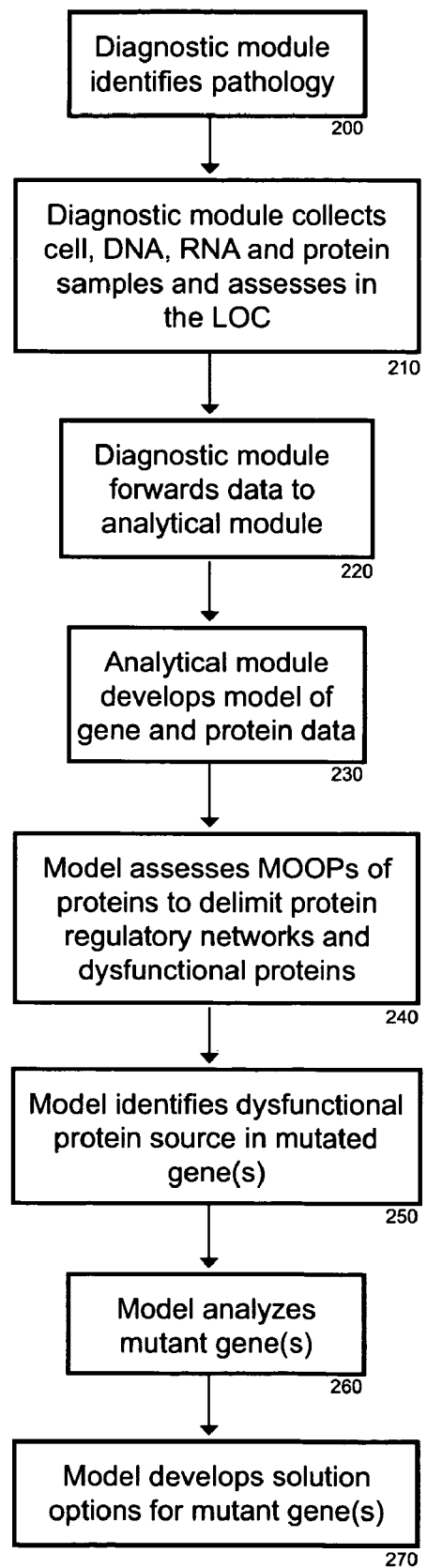
FIG. 2 is a flow chart describing the process of collecting sample data and modeling the data using iMD modules.

FIG. 2 shows the process of collecting sample data and modeling the data using iMD modules. After the diagnostic module identifies pathology (200), it collects cell, DNA, RNA and protein samples and assesses them in the LOC (210). The diagnostic module then forwards the data to the analytical module (220), which develops a model of gene and protein data (230). The model assesses multi-objective optimization problems (MOOPs) of the proteins to delimit the protein regulatory network and dysfunctional proteins (240). The model identifies the dysfunctional protein source(s) in mutated gene(s) (250) and analyzes the mutant gene(s) (260). The model then develops solution options for mutant gene(s) (270).

Figure 3:
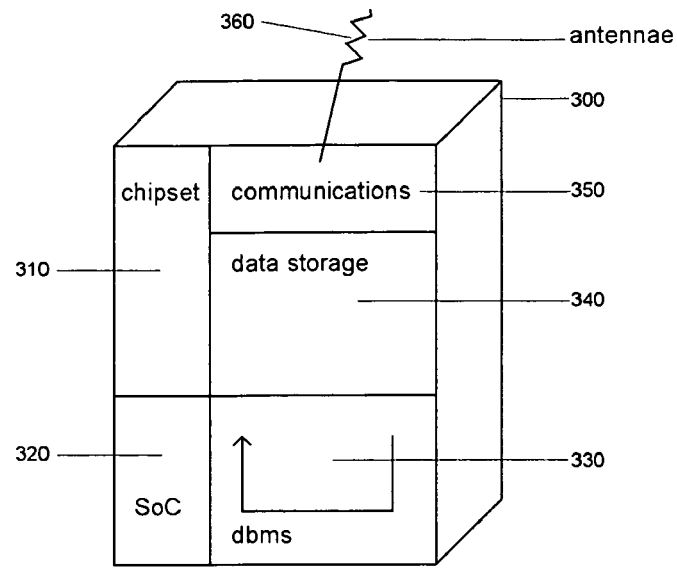
FIG. 3 is a schematic diagram showing a 3D view of the analytical module architecture.

FIG. 3 shows a 3D view of the analytical module architecture. The analytical module (300) consists of an SoC (320), a chip set (310), a database management system (dbms) (330), communications (350), an antennae (360) and data storage (340). The analytical module is integrated into an iMD to coordinate the modeling and analysis process by obtaining data from the diagnostic module(s) experimentation on biological samples. The modeling data is then forwarded to therapeutic module(s) for administration of solution options.

Figure 4:
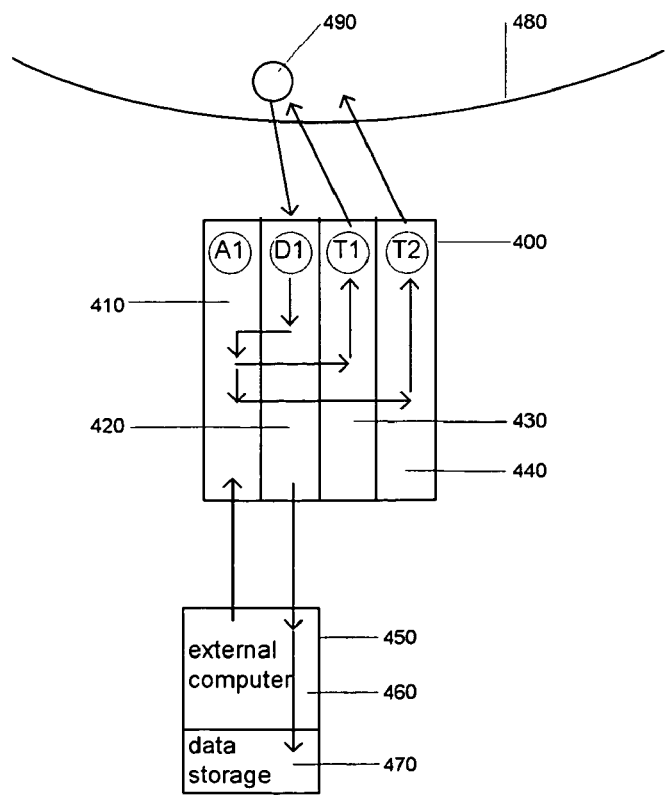
FIG. 4 is a schematic diagram showing how software agents perform functions in the functional modules of an iMD to solve a problem with a pathology.

FIG. 4 shows how software agents perform functions in the functional modules of an iMD to solve a problem with a pathology. The iMD (400) consists of the analytical module (410), diagnostic module (420) and therapeutic modules (430 and 440). Once cell samples are collected at 490 and analyzed in the LOC of the diagnostic module, the data is transferred by using software agents to the analytical module. The analytical module then uses software agents to model the data, develop solution options for pathology and forward the data to the therapeutic modules. The therapeutic modules organize and deliver the solution(s) to the tissue (480). Software agents from the iMD analytical module also interact with external computation (460) and data storage (470) capabilities.

Figure 5:
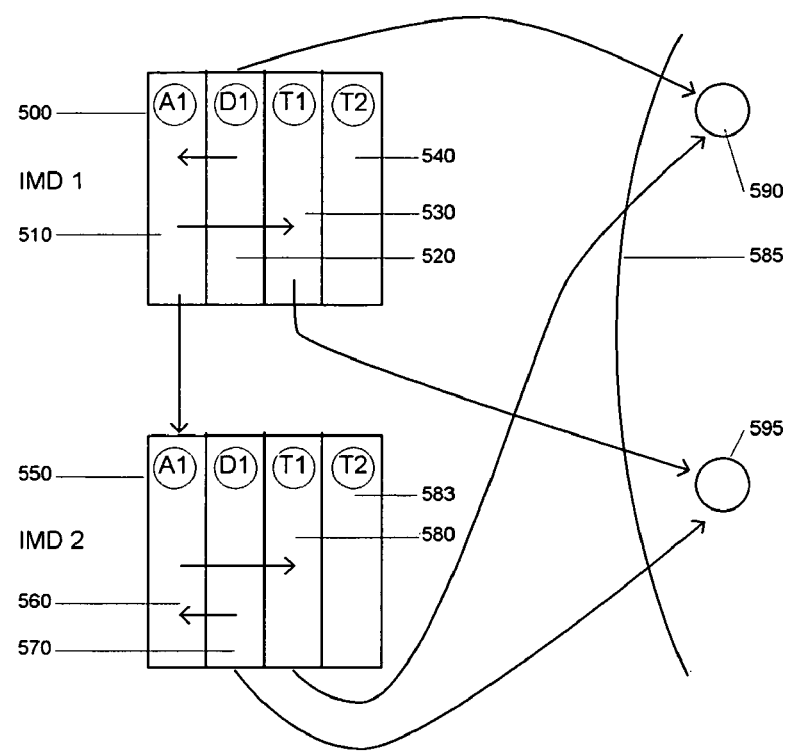
FIG. 5 is a schematic diagram showing how two iMDs exchange data with software agents to solve simultaneous problems.

FIG. 5 shows how two iMDs exchange data with software agents to solve simultaneous problems. Probes are sent from iMD 1 (500) diagnostic module 1 (520) to extract cell samples from a cell site (590) and from iMD 2 (550) diagnostic module 1 (570) to extract cell samples from a cell site (595) in tissue 585. The diagnostic modules analyze the cell samples in their LOCs and the software agents pass the data from the diagnostic modules to the analytical modules (510) and 560) of each iMD. Software agents are used to exchange data between the analytical modules. The analytical modules use software agents to build models of the diseases. The model from iMD 1 requires therapies that are in iMD 2 and the software agents detect the substance availability and transfer the solution option to iMD 2 therapeutic module 1 (580), which applies the solution to cell site 590. Similarly, the model from iMD 2 requires therapies that are in iMD 1 and the software agents detect the substance availability and transfer the solution option to iMD 1 therapeutic module (530), which applies the solution to cell site 595.

Figure 6:
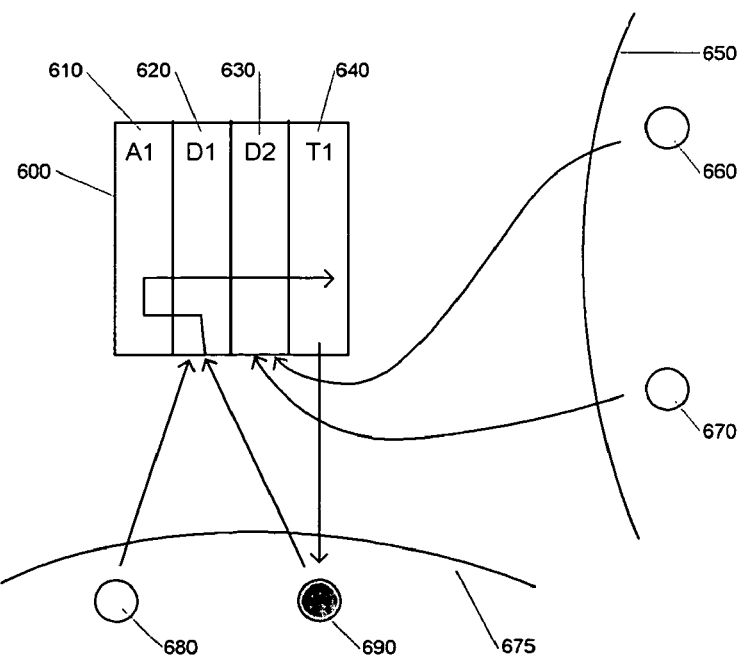
FIG. 6 is a schematic diagram showing how two competitive software agent teams operate, with the winning team showing demonstrable results.

FIG. 6 shows two competitive software agent teams, with the winning team showing demonstrable results. Cell samples from a cell sites (680 and 690) in a tissue (675) are collected by probes and delivered to diagnostic module 1 (620), while cell samples from two cell sites (660 and 670) in another tissue (650) are collected by probes and delivered to diagnostic module 2 (630). The samples are analyzed by the LOCs on each diagnostic module and the data are transferred by different teams of software agents. Each team—one from diagnostic module one and another from diagnostic module two—builds a model at the analytical module (610) as new information from each diagnostic module LOC is input. The software agents compete to build the model by using hybrid metaheuristics that allow them to achieve a goal (that is, a time constrained) based solution. The software agent team that administers the cell data from the cell site at 690 completes the model first and sends the solution options for a remedy to the therapeutic module (640), which combines elements for application to the cell site. The therapeutic module then applies the solution to the cell site at 690.

Figure 7:
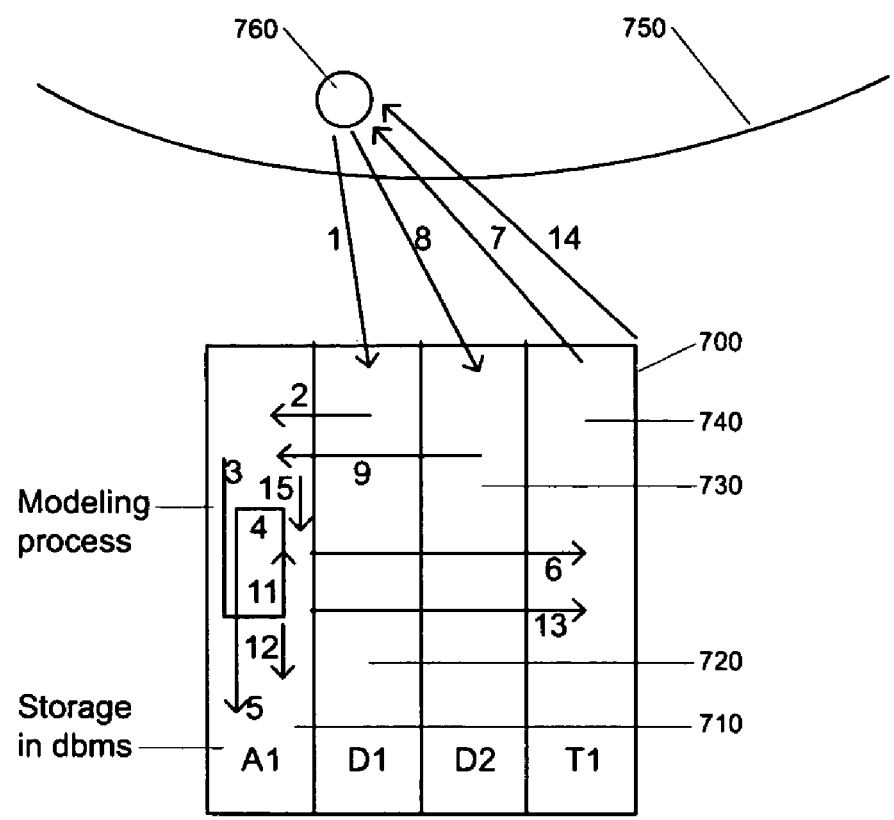
FIG. 7 is a schematic diagram showing the diagnostic refinement and therapeutic process facilitated by software agents.

FIG. 7 shows the diagnostic refinement and therapeutic process facilitated by software agents. Once cell samples are collected from a cell site (760) and transferred to the diagnostic module (720), the samples are analyzed in a LOC and software agents transfer the data to the analytical module (710). The software agents facilitate the building of a model and enter the model into a database for storage. The agents then transfer the solution options from the model to the therapeutic module (740) for composition and delivery of a remedy to the cell site. The remedy is evaluated by collecting samples from the tissue site (750) and analyzing the samples in diagnostic module 2 (730). The software agents facilitate the building of a updated model and enter the updated model into a database for storage. The agents then transfer the updated solution options to the therapeutic module, which makes refinements to the original solution and administers an updated remedy to the cell site. The pathology is then solved or managed.

Figure 8:
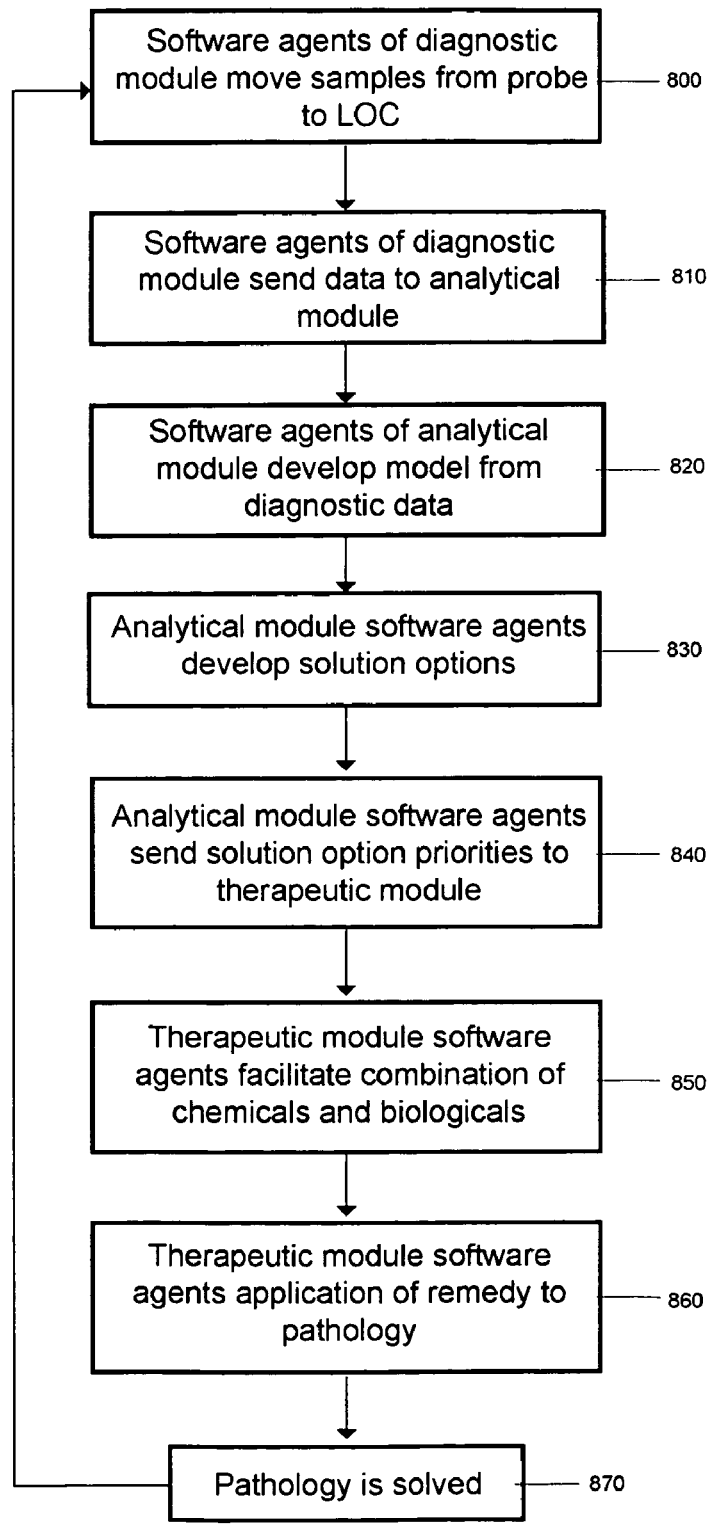
FIG. 8 is a flow chart describing the process of an iMD solving problems using software agents in the diagnostic, analytical and therapeutic modules.

FIG. 8 shows the process of an iMD solving problems using software agents in the diagnostic, analytical and therapeutic modules. Software agents in the diagnostic module coordinate the process of moving cell samples from the probes to the LOC (800). After the diagnostic module tests the samples, the software agents of the diagnostic module send the data to the analytical module (810). Software agents of the analytical module develop a model from diagnostic data (820) and develop solution options (830). The analytical module software agents send solution option priorities to the therapeutic module (840). The therapeutic module software agents facilitate the combination of chemicals and biologicals into a remedy (850), facilitate the application of the remedy to the pathology (860) and the pathology is solved (870).

Figure 9:
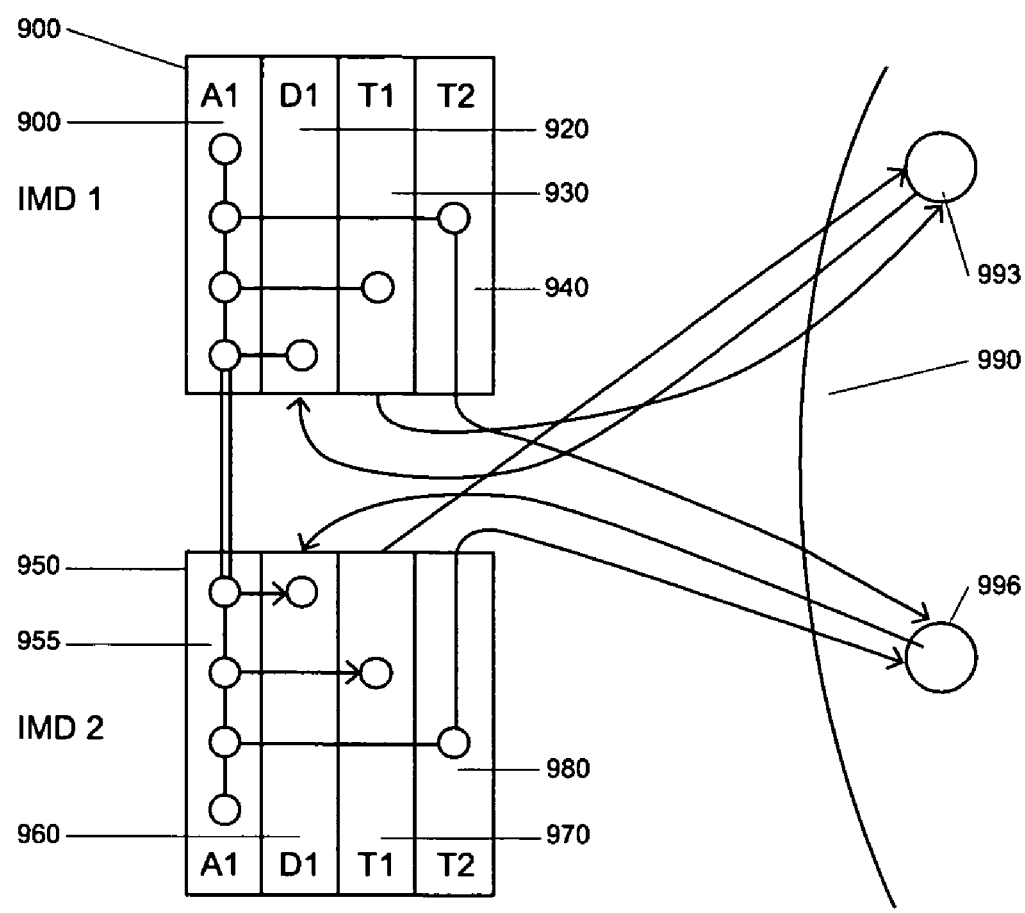
FIG. 9 is a schematic diagram showing the software agent packets moving from location to location to facilitate diagnosis, modeling and remedies of two pathologies by two iMDs simultaneously.

FIG. 9 shows the software agent packets moving from location to location to facilitate diagnosis, modeling and remedies of two pathologies by two iMDs simultaneously. Cell samples are collected from two locations (993 and 996) in a tissue (990) and are transferred to iMD 1 (900) diagnostic module 1 (920) and iMD 2 (950) diagnostic module 1 (960). The diagnostic modules analyze the samples in their LOCs. Software agents collect the LOC data analysis and transfer the data to the analytical modules (910 and 955), coordinate the building of models and transfer the best available solution options to the therapeutic modules (930, 940, 970 and 980). The analytical modules of the two iMDs work together to share information by using the software agents to retrieve and transfer data. The therapeutic modules each develop separate remedies by combining biological and chemical elements into customized therapies as specified by the models. These processes are coordinated by the software agents, which activate sensors, valves and compartments to combine specific elements for each remedy. The remedies are then applied to the cell sites. In this example, iMD 1 T1 and iMD 2 T1 apply their remedies to 993 while iMD 1 T2 and iMD 2 T2 apply their remedies to 996.

Figure 10:
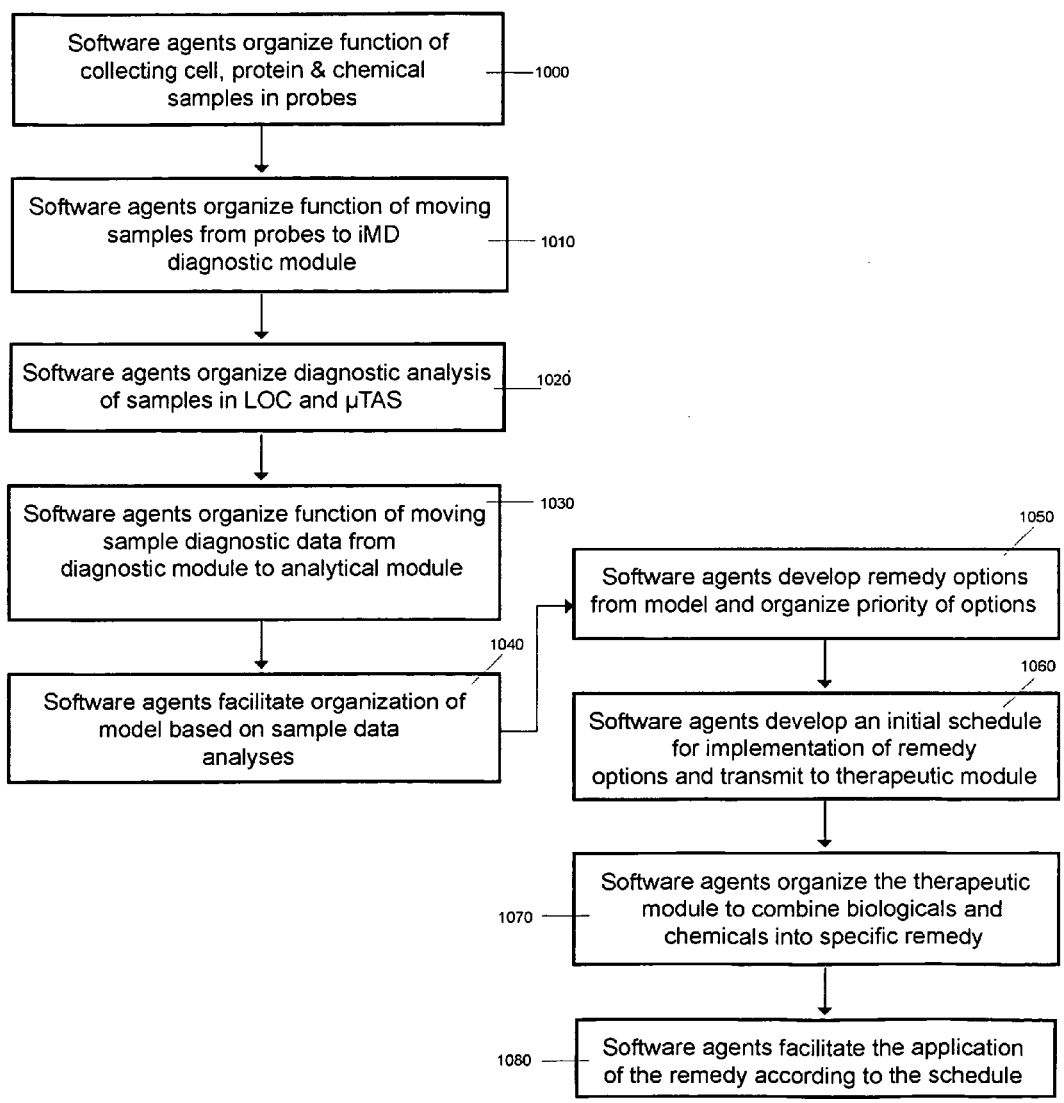
FIG. 10 is a flow chart describing the process of software agents building a model in the analytical module from data acquired and analyzed in the diagnostic module and applying the model in the therapeutic module of the iMD.

FIG. 10 shows the process of software agents building a model in the analytical module from data acquired and analyzed in the diagnostic module and applying the model in the therapeutic module of the iMD. After the software agents organize the function of collecting cell, protein and chemical samples in probes (1000), they organize the function of moving samples from the probes to the diagnostic module of an iMD (1010). The software agents organize diagnostic analysis of samples in the LOC and µTAS (1020) and organize the function of moving sample diagnostic data from the diagnostic module to the analytical module (1030). The software agents then facilitate the organization of a model based on sample data analyses (1040), develop remedy options from the model and organize the priority of options (1050). The software agents develop an initial schedule for implementation of remedy options and transmit them to the therapeutic module (1060). The software agents then organize the therapeutic module to combine biologicals and chemicals into a specific remedy (1070). The software agents facilitate the application of the remedy according to a schedule (1080) as specified by the model. As priorities change, the initial schedule is modified.

Figure 11:
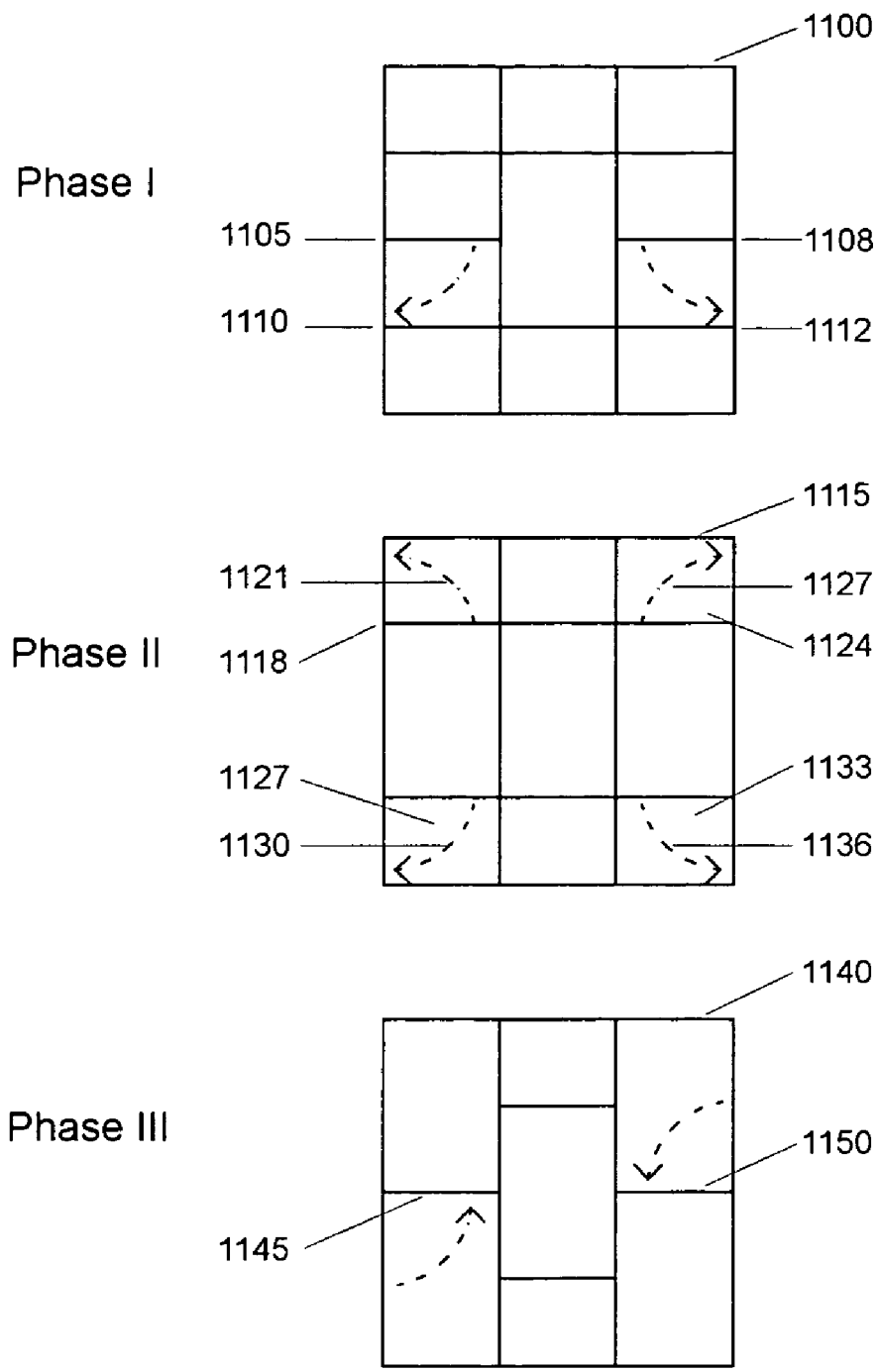
FIG. 11 is a set of schematic diagrams showing the process of software agents activating the therapeutic module architecture transformation process in an iMD.

FIG. 11 shows the process of software agents activating the therapeutic module architecture transformation process in an iMD. In phase I, the therapeutic module (1100) is structured with several compartments as shown. Software agents facilitate the movement of the compartment barriers at 1105 and 1112. The barriers on the right and left sides fold down flush with the vertical wall by using a movable joint. In phase II, software agents facilitate the movement of the compartment barriers at 1118, 1127, 1124 and 1133. The barriers on the right and left side compartments fold down. Finally, in phase three, the barriers at 1145 and 1150 are activated by the software agents to be folded up into position as shown. The hardware restructuring process, coordinated by the software agents, allows the therapeutic module to customize specific therapies to solve novel problems.

Figure 12:
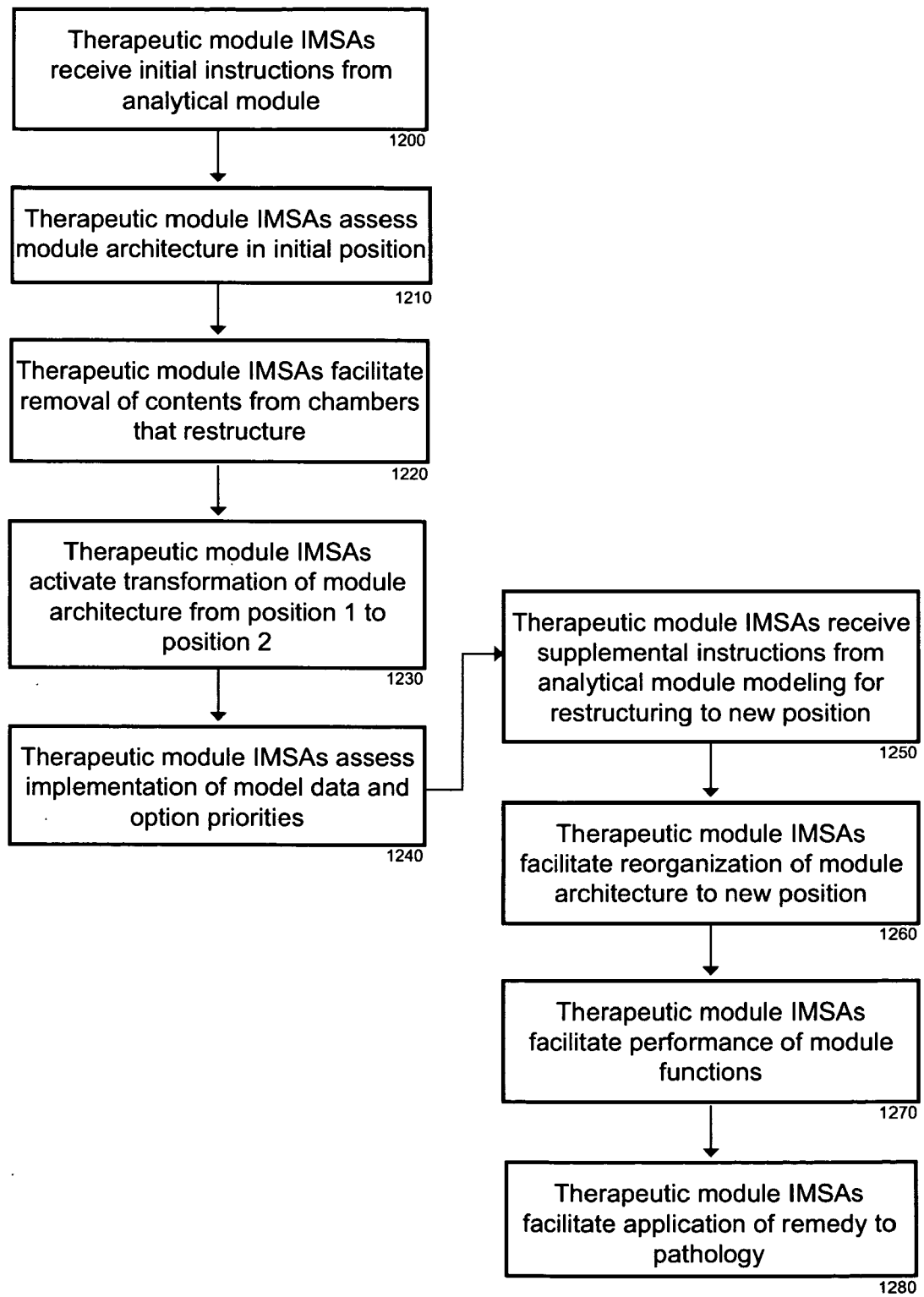
FIG. 12 is a flow chart describing the process of software agents organizing and reorganizing the therapeutic module of the iMD.

FIG. 12 shows the process of software agents organizing and reorganizing the therapeutic module of the iMD. The therapeutic module software agents receive initial instructions from the analytical module (1200) and assess module architecture in an initial position (1210). The therapeutic module software agents facilitate removal of contents from chambers that restructure (1220) and software agents activate the transformation of the module architecture from position one to position two (1230) as specified by the model. The therapeutic module software agents assess the implementation of the model data and option priorities (1240) and receive supplemental instructions from the analytical module modeling for restructuring to new position (1250). The therapeutic module software agents then facilitate the reorganization of module architecture to a new position (1260) and facilitate the performance of module functions (1270). The therapeutic module software agents facilitate application of a remedy to pathology (1280).

Figure 13:
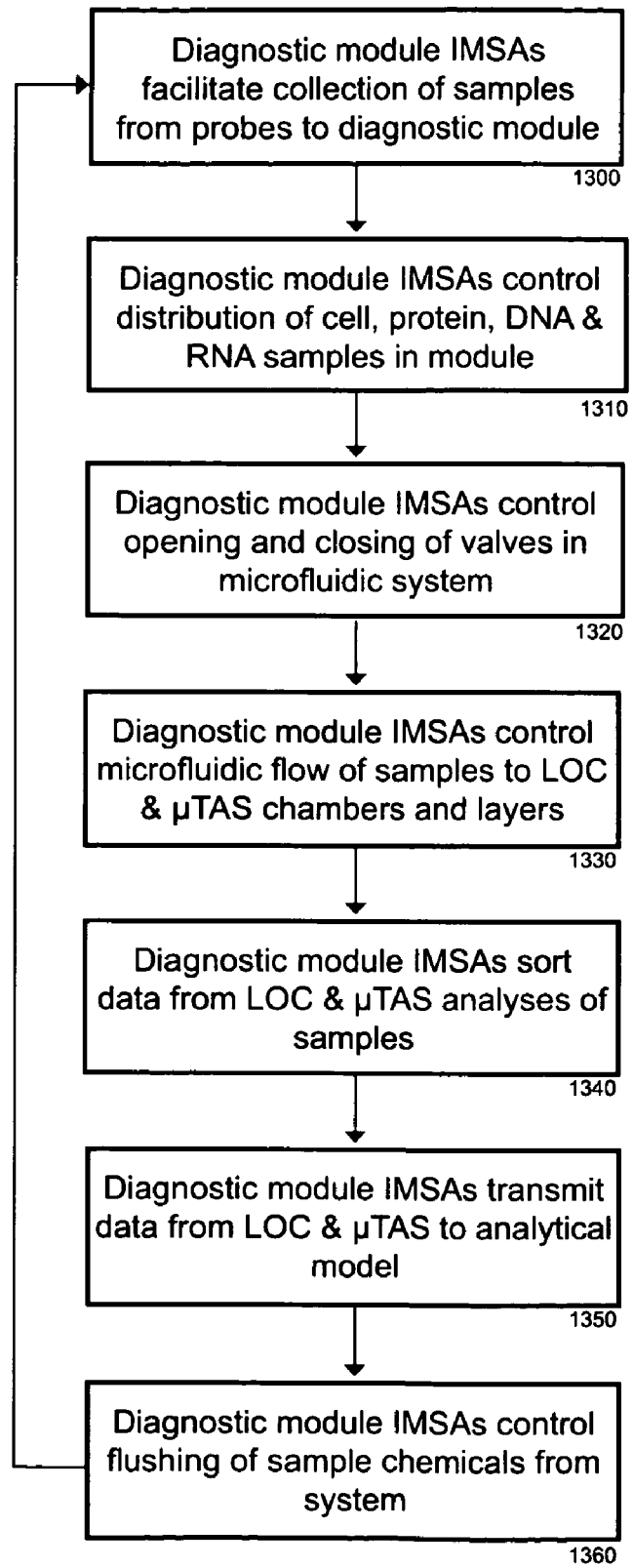
FIG. 13 is a flow chart describing the process of using software agents to collect and analyze biological and chemical samples in the diagnostic module of the iMD.

FIG. 13 shows the process of using software agents to collect and analyze biological and chemical samples in the diagnostic module of the iMD. The diagnostic module software agents facilitate collection of samples from probes to diagnostic module (1300) and software agents control the distribution of cell, protein, DNA and RNA samples in the module (1310). The diagnostic module software agents control the opening and closing of valves in the microfluidic system (1320) and control the microfluidic flow of samples to the LOC and µTAS chambers and layers (1330). The diagnostic module software agents sort data from the LOC and µTAS analyses of samples (1340) and transmit data from the LOC and µTAS to the analytical module (1350). The diagnostic module software agents control the flushing of sample chemicals from the system (1360) and the process repeats.

Figure 14:
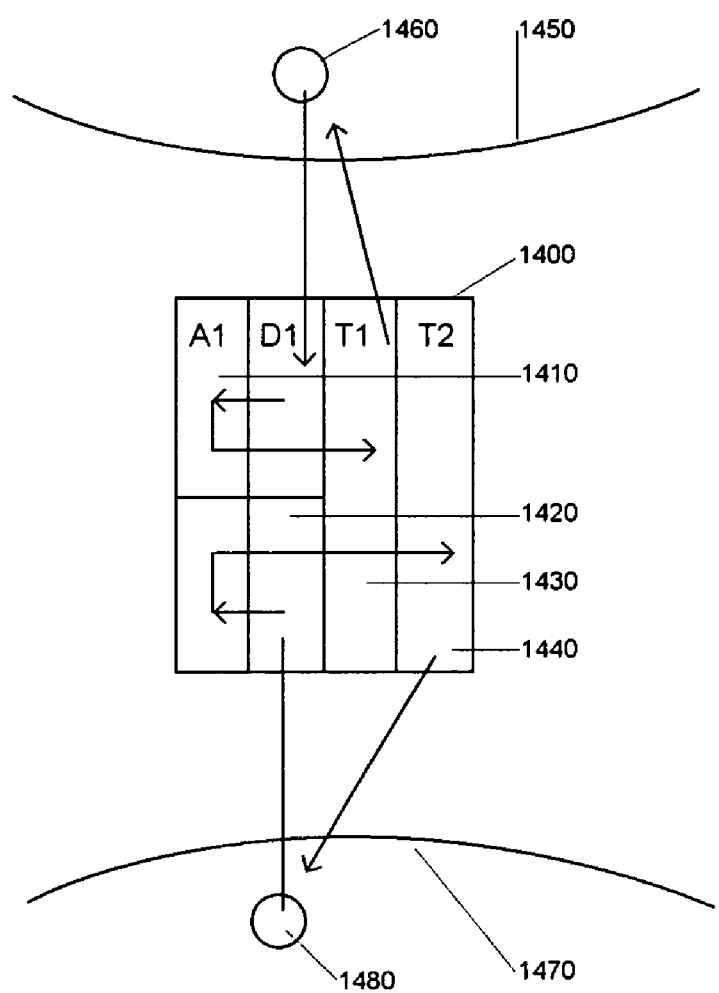
FIG. 14 is a schematic diagram showing software agents facilitating two parallel simultaneous operations in an iMD.

FIG. 14 shows the software agents facilitating two parallel simultaneous operations in an iMD. Cell samples are collected from different cells sites (1460 and 1480) in different tissues (1450 and 1470) and input into the diagnostic module (1420). The diagnostic module tests the samples in the LOC and the µTAS and software agents transfer the data results to the analytical module (1410) for construction of two separate models. Software agents then forward the solution options from each module to therapeutic modules 1 (1430) and 2 (1440) for construction of remedies and application of the solutions to the cell clusters of the different tissues.

Figure 15:
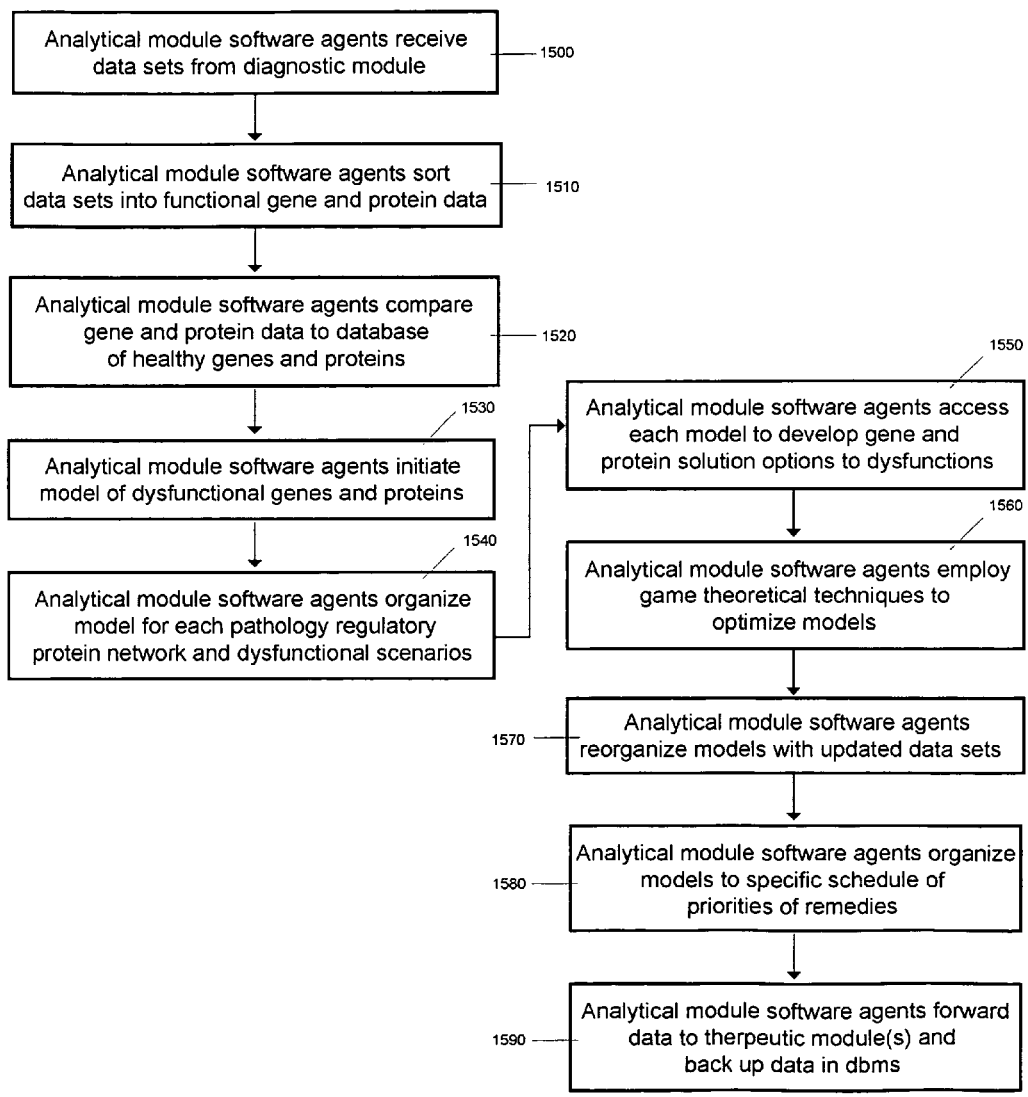
FIG. 15 is a flow chart describing the process of analytical module software agent operations in an iMD.

FIG. 15 shows the process of analytical module software agent operations in an iMD. Once the analytical module software agents receive data sets from the diagnostic module (1500), they sort data sets into functional gene and protein data (1510). The software agents compare gene and protein data to a database of healthy genes and proteins (1520) and initiate construction of a model of dysfunctional genes and proteins (1530). The software agents then organize a model for each pathology regulatory protein network and dysfunctional scenarios (1540). The analytical module software agents then access each model to develop gene and protein solution options to dysfunctions (1550) and employ game theoretical techniques to optimize the models (1560). The software agents reorganize the models with updated data sets (1570) and organize the models to a specific schedule of priorities of remedies (1580). The software agents then forward the data to the therapeutic module(s) and back up the data in the database management system (1590).

Figure 16:
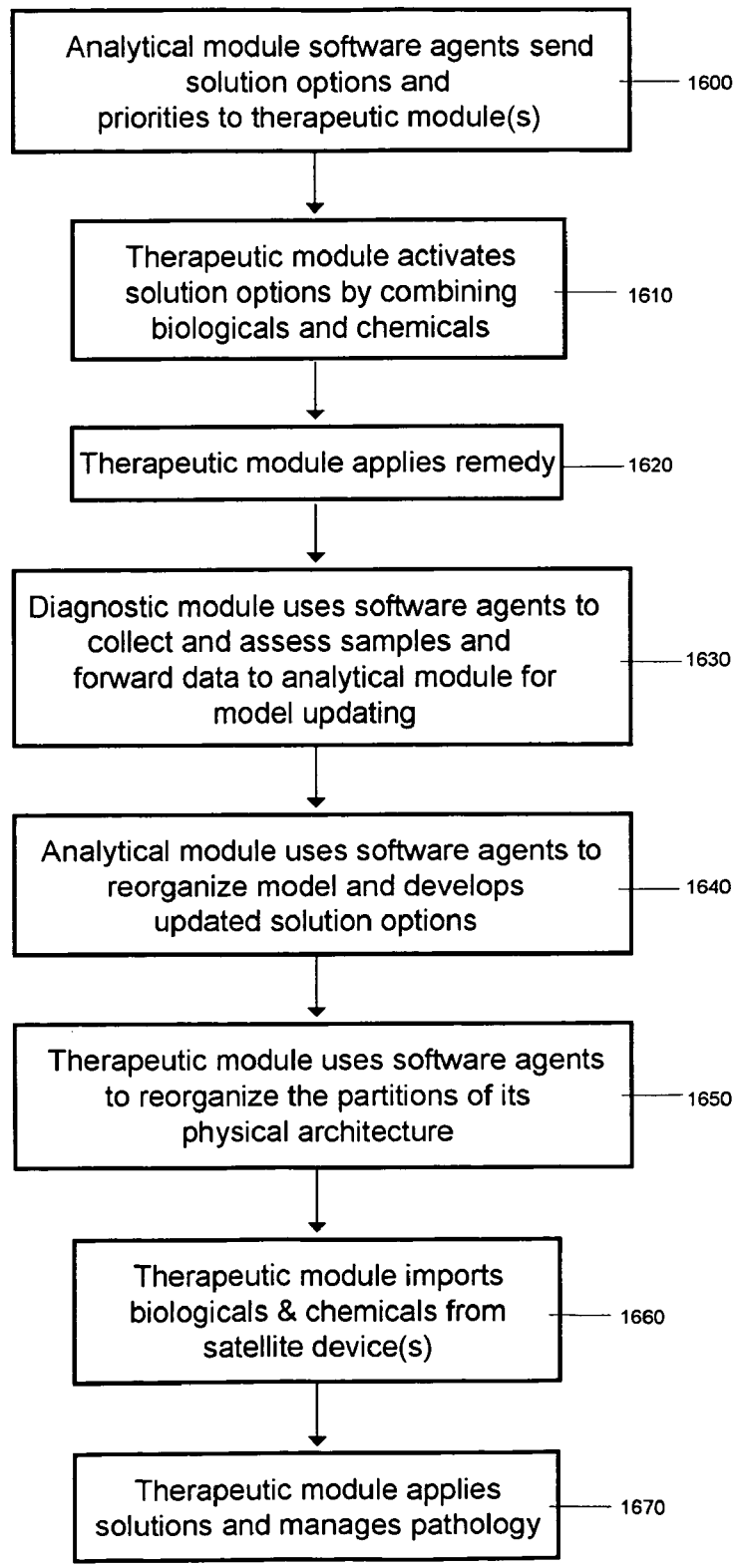
FIG. 16 is a flow chart describing the process of assessing the application of a remedy and refining the model for therapy to manage a pathology using an iMD.

FIG. 16 shows the process of assessing the application of a remedy and refining the model for therapy to manage a pathology using an iMD. After the analytical module software agents send solution options and priorities to the therapeutic module(s) (1600), the therapeutic module software agents activate solution options by combining biologicals and chemicals (1610). The therapeutic module applies the remedy (1620) and the diagnostic module uses software agents to collect and assess samples and forward the test data to the analytical module for model updating (1630). The analytical module software agents reorganize the model and develop updated solution options (1640). The therapeutic module uses software agents to reorganize the partitions of its physical architecture (1650) and the therapeutic module imports biologicals and chemicals from satellite device(s) (1660). The therapeutic module applies solutions and manages the pathology (1670).

Figure 17:
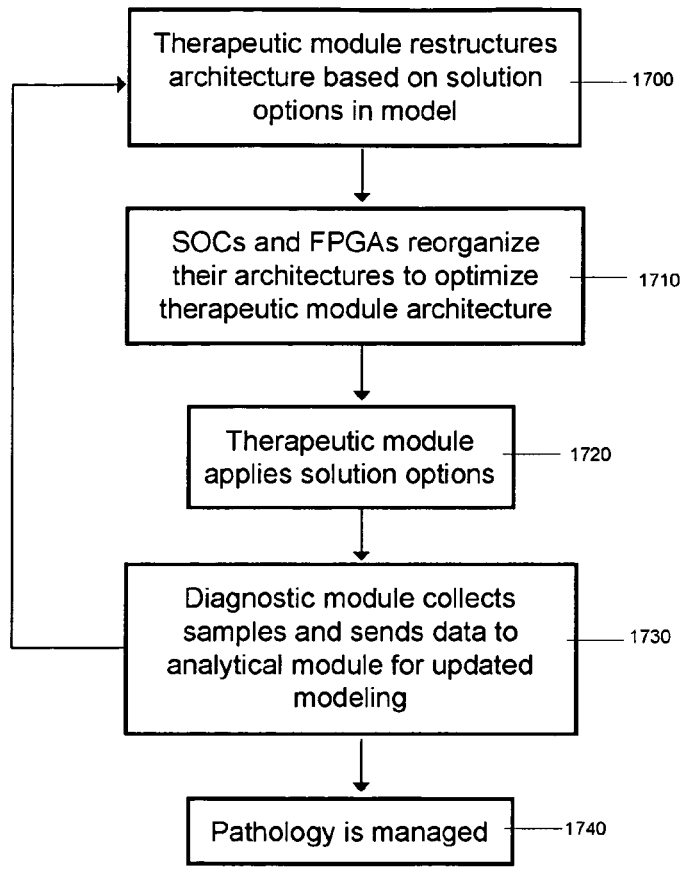
FIG. 17 is a flow chart describing the process of restructuring the architecture of the therapeutic module to optimize solutions to problems using an iMD.

FIG. 17 shows the process of restructuring the architecture of the therapeutic module to optimize solutions to problems using an iMD. Once the therapeutic module restructures its architecture based on solution options in the analytical model (1700), the SoCs and FPGAs reorganize their architectures to optimize therapeutic module architecture orientation (1710). The therapeutic module applies solution options (1720) and the diagnostic module collects samples and sends data to the analytical module for updated modeling (1730) and the process repeats. The pathology is managed (1740).

Figure 18:
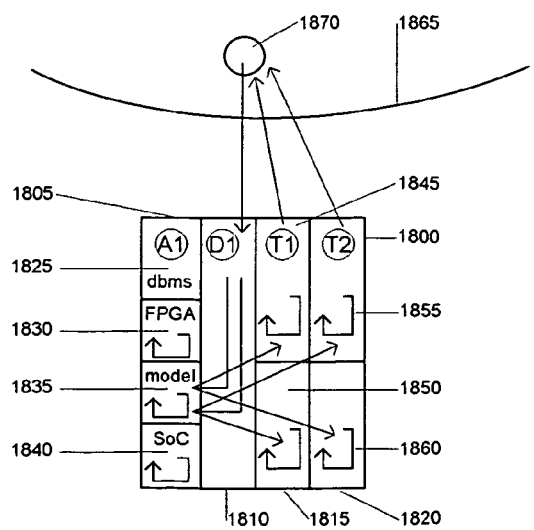
FIG. 18 is a schematic diagram showing the co-adaptation of iMD components and semiconductors in which the analytical and therapeutic modules co-evolve the restructuring of their components with the semiconductor evolvable hardware reconfiguration in an iMD.

FIG. 18 shows the co-adaptation of iMD hardware and chip hardware in which the analytical and therapeutic modules co-evolve the restructuring of their components with the semiconductor evolvable hardware reconfiguration in an iMD. After cell samples are imported from a cell site (1870) to the diagnostic module (1810) and the diagnostic module LOC and µTAS evaluates the samples, the data is sent to the analytical module (1805) by software agents as the data is collected. The analytical module builds a model (1835) with software agents. As the model is built, the SoC (1840) and FPGAs (1830) restructure their configurations in order to optimize the performance of the model. The restructuring process of the semiconductor hardware is facilitated with software agents. The model generates solution options, which are transferred by software agents to the four distinct compartments (1845, 1850, 1855 and 1860) of the therapeutic modules (1815 and 1820). In order to accommodate the solution options, the compartments of the therapeutic modules restructure their configurations. Once the solution options are constructed, the remedies are applied to the cell site for treatment. As the refinement of the solution is processed by the iMD, the SoC (and FPGAs) and the therapeutic modules' architectures continue to restructure to optimize the performance of the system to deliver the appropriate customized and refined therapy to solve the pathology. This process of hardware co-evolvability continues until the disease is solved or managed.

The therapeutic module is capable of reconfiguration. There are two main models used for reconfiguration. The first is the change from preset one position to another preset position, much like an FPGA changes from one ASIC position to another ASIC position. In the case of the therapeutic module of the iMD, however, the transformation of the module components involves changing the structure of the microfluidic compartments to maximize their effects in different situations. The second main reconfiguration model is continuously programmable, without the use of preset configurations. In this sense, the therapeutic module uses the SoC, metaheuristics and EDA software to continuously reorganize the structure of the microfluidic compartments or the layers of the device. In one embodiment, this process of continuous transformation occurs while the device is in operation by closing down some components for restructuration while the others are fully operational.

The continuous programmable features of the therapeutic module restructuration processes represent a form of advanced prototyping of solutions to complex diseases. The co-adaptation of the SoC (or FPGAs) with the therapeutic module facilitates evolvable device applications. In this sense, the therapeutic module is an evolvable reprogrammable microfluidic biochip (ER-PROM). Each custom solution to a complex biomedical optimization problem represents a distinct therapy. It is, perhaps, ironic, that each unique solution developed by an iMD to solve a unique biomedical problem is itself patentable, much like IP cores for FPGAs. In this sense, the biomedical research community will use the iMD as a research tool for therapeutic solution generation.

Figure 19:
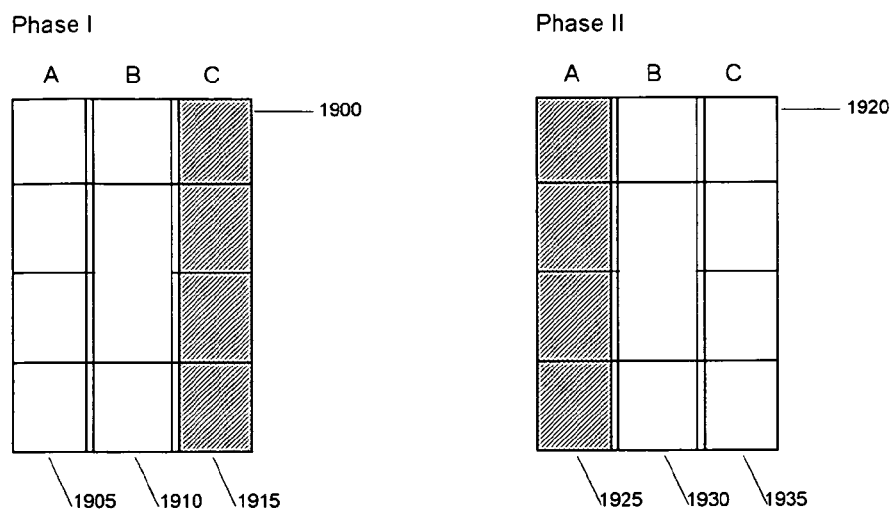
FIG. 19 is a schematic diagram showing two phases of a process of restructuring part of a therapeutic module of an iMD while other parts of the therapeutic module are operational, thereby allowing for continuous operation.

FIG. 19 shows the two phases of a process of restructuring part of a therapeutic module of an iMD while other parts of the therapeutic module are operational, thereby allowing for continuous operation. In the first phase, the therapeutic module software agents stop "C" column processes from functioning by temporarily shutting it down and transferring its chemicals and biologicals to other compartments in order to provide the opportunity for restructuring. Column "C" compartments then restructure to satisfy the model reconfiguration mode. Once reconfigured, the "C" column of compartments is operational, as in phase II. However, column "A" stops functioning, transfers its biologicals and chemicals to other compartments and engages in a reconfiguration process to satisfy the model constraints. Once reconfigured, it activates the functioning and combines elements for activating the remedy composition for satisfying the model solution options. The advantage of this approach is that some parts of the therapeutic module are on-line as other parts restructure. This process is analogous to some types of FPGAs.

Figure 20:
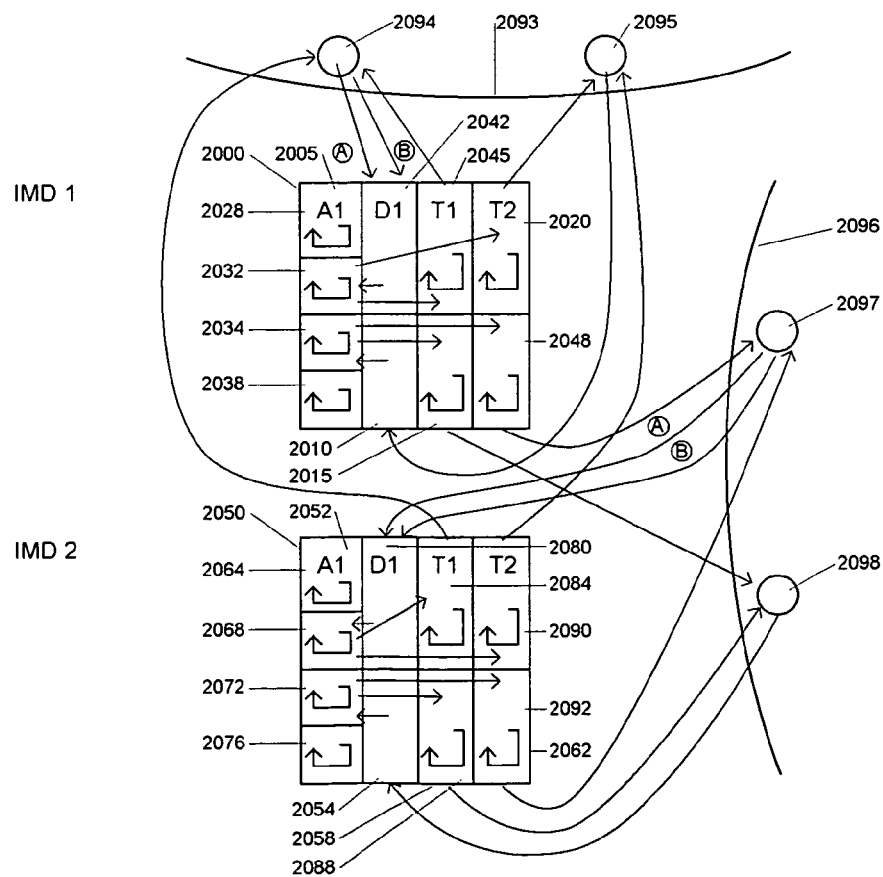
FIG. 20 is a schematic diagram showing the simultaneous sequential restructuring of two iMDs to solve multiple pathologies.

FIG. 20 shows the simultaneous sequential restructuring of two iMDs to solve multiple pathologies. Two iMDs (2000 and 2050) collect cell samples (at 2094 and 2097) at two different tissues (2093 and 2096). IMD 1 diagnostic module (2042) processes two cell samples (A and B) in its LOC and μTAS, while the iMD 2 diagnostic module (2080) processes two cell samples (A and B) in its LOC and μTAS. Software agents retrieve the test data about the cell samples and forward the data to the analytical modules (2005 and 2052) of the iMDs. The analytical modules restructure their SoCs and FPGAs to optimize construction of their models by using software agents. Solution options from the models are transmitted by software agents to the therapeutic module components (2015, 2045, 2048 and 2020 in iMD 1 and 2058, 2084, 2090 and 2092 in iMD 2). The therapeutic module components engage in reconfiguration of each chamber as specified in the computer models to construct the optimal remedies for the pathologies. Once configured to the optimal architecture, the therapeutic modules' compartments combine the biologicals and chemicals into specified remedies and apply the remedies to the cell sites (2094, 2095, 2097 and 2098). The process continues as the remedies are refined and the pathologies are ultimately solved or managed.

FIG. 21 shows FPGAs on each layer of the therapeutic module in an iMD restructuring each layer and the FPGAs in a sequence of operational phases. In phase I, the FPGAs integrated into the therapeutic module (2127, 2130 and 2133) restructure to a specific configuration and activate the restructuring process of specific chambers of the therapeutic module. The dividers at 2105, 2110, 2115, 2120 and 2125 are folded down in this initial phase. In phase II, the FPGAs (2153, 2155 and 2158) continue to reconfigure their structures to optimize the therapeutic module restructuring process. At this point, the therapeutic module compartment dividers are resurrected to the positions shown at 2137, 2140, 2145 and 2150. In phase III, the FPGAs (2175, 2178 and 2182) are again reconfigured to new hardware configurations. In this final phase, the dividers of the therapeutic module compartments are again reconfigured to positions at 2163, 2172, 2167 and 2168. In this configuration, the therapeutic module is able to optimally satisfy the constraints of the model to construct customized remedies.

Figure 22:
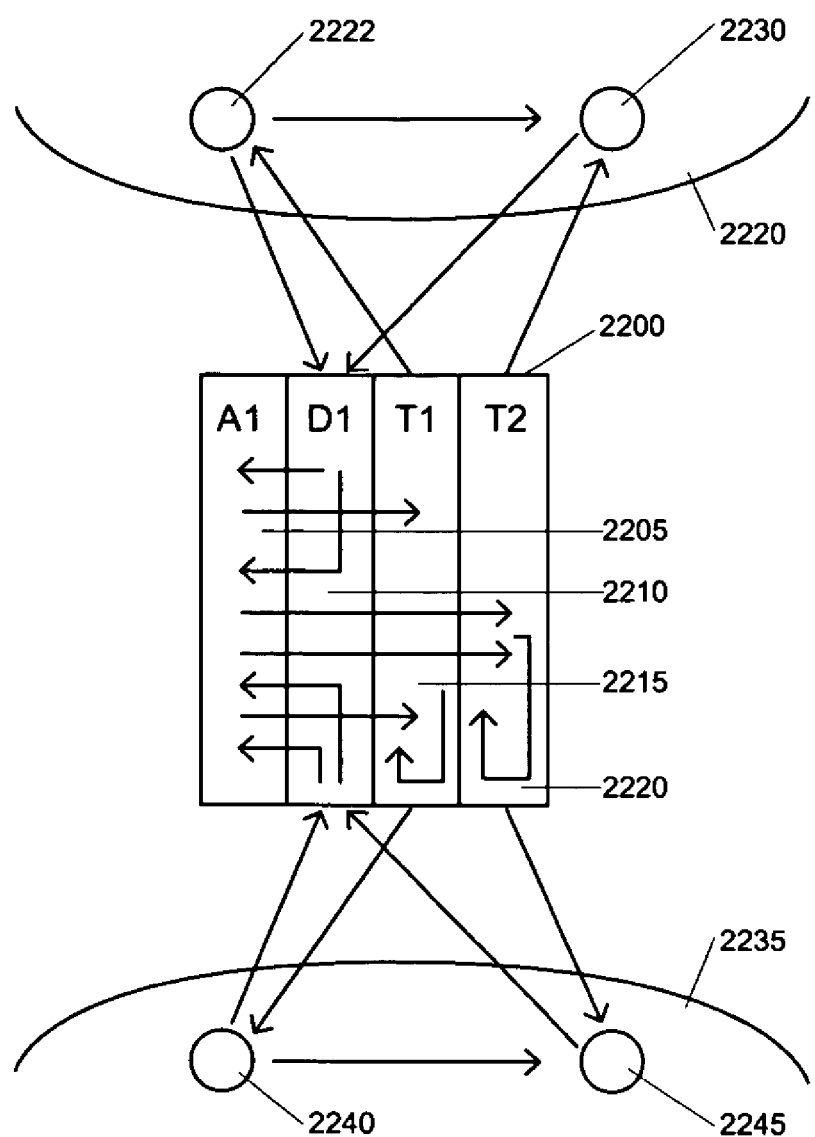
FIG. 22 is a schematic diagram showing how an iMD adapts to multiple evolving pathologies as its environment changes by transforming in a later phase to remedy a changed pathology.

As diseases evolve, it is necessary for the iMD to co-evolve its computing and therapeutic components to optimize remedy solutions to solve complex pathologies. This process is shown in FIG. 22 as an iMD adapts to multiple evolving pathologies as its environment changes by transforming in a later phase to remedy a changed pathology. Cell samples from multiple sites (2222 and 2240) in different tissues (2220 and 2235) are collected and analyzed by the diagnostic module (2210) of the iMD (2200). Software agents forward the testing data from the LOC and μTAS of the diagnostic module to the analytical module. Software agents facilitate model building of the data in the analytical module and forward the solution options to therapeutic module 1 (2115). Therapeutic module 1 then constructs remedies and applies them to the initial cell sites (2222 and 2240). However, the patient condition evolves and the condition of the cells changes. The iMD collects cell samples from nearby locations in the tissues (2230 and 2245) and tests the samples in the diagnostic module LOC and μTAS, the data from which is transferred by software agents to the analytical module, which constructs updated models of the pathologies. These updated models are forwarded to the therapeutic modules with the assistance of software agents, which administer the restructuring process to reconfigure the therapeutic module compartments to optimize the refined and updated remedy protocols. After the therapeutic modules have reconfigured their structures and combined specific biological and chemical elements into updated remedies, these remedies are applied to the evolved pathologies at 2230 and 2245 in order to solve or manage the diseases.

Figure 23:
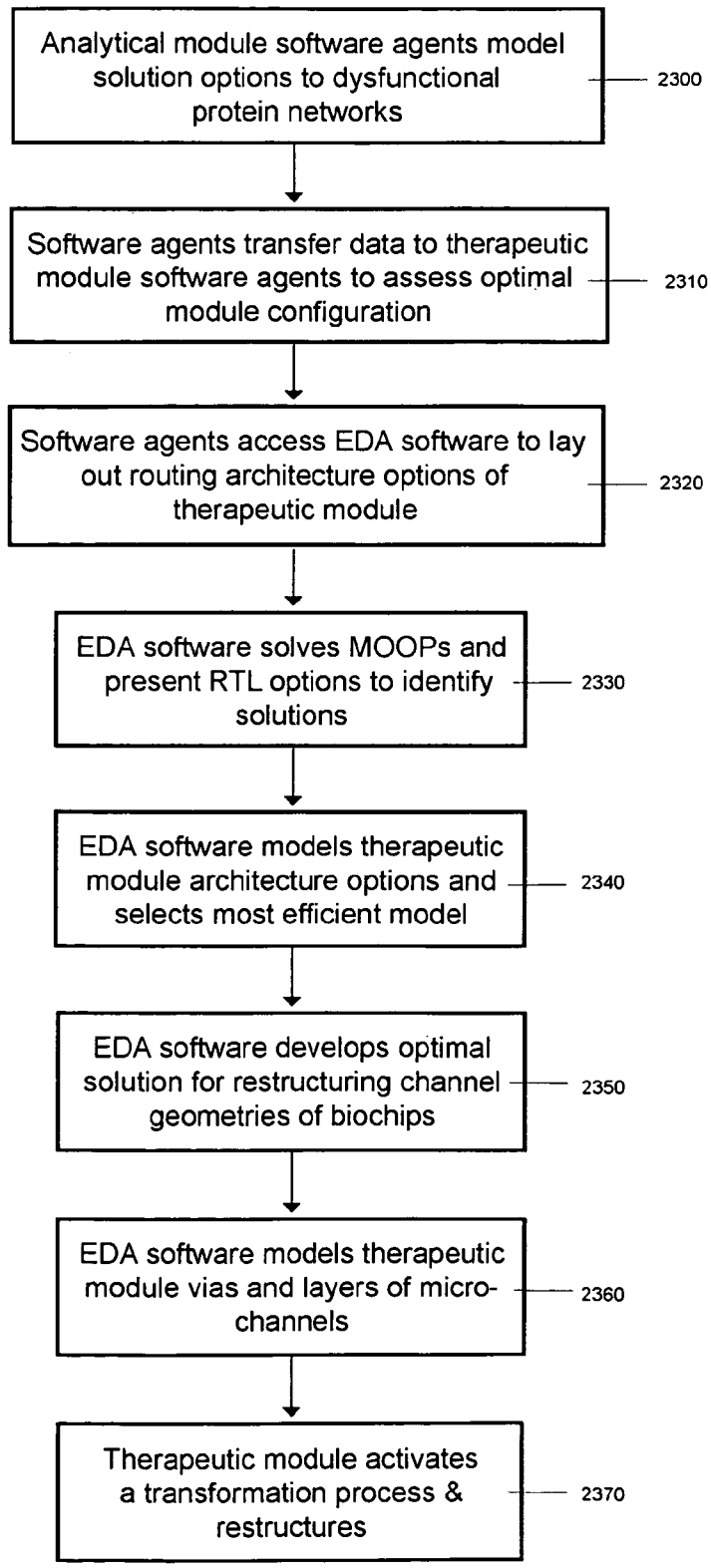
FIG. 23 is a flow chart describing the process of using EDA software to guide the reorganization of a therapeutic module architecture in an iMD.

FIG. 23 shows the process of using EDA software to guide the reorganization of a therapeutic module architecture in an iMD. After the analytical module software agents model solution options to dysfunctional protein networks (2300), the software agents transfer data to the therapeutic module software agents to assess optimal module configuration (2310). The software agents access EDA software to lay out routing architecture options for the therapeutic module (2320). The EDA software solves multi-objective optimization problems (MOOPs) and presents RTL options to identify solutions (2330). The EDA software models therapeutic module architecture options, selects the most efficient model (2340) and then develops an optimal solution for restructuring channel geometries of biochips (2350). The EDA software models the therapeutic module vias and layers of micro-channels (2360) and the therapeutic module activates a transformation process (2370). The therapeutic module then restructures its configuration.

Figure 24:
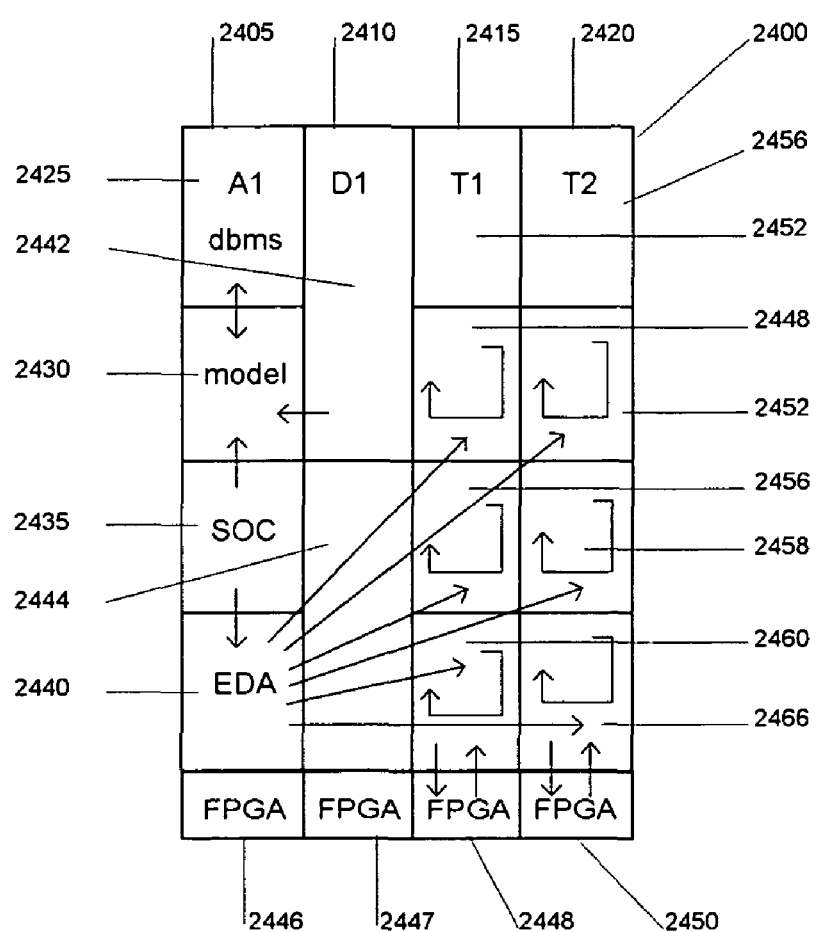
FIG. 24 is a schematic diagram showing how EDA software restructures therapeutic module components in an iMD.

FIG. 24 shows how EDA software restructures therapeutic module components in an iMD. The SoC (2435) in the analytical module (2405) controls the modeling process (2430) and coordinates the EDA software (2440) to co-develop a model to reconfigure the therapeutic module(s) (2415 and 2420) hardware structures. Once the analytical module models the therapeutic options, the EDA software configures the optimal hardware configurations. The therapeutic module(s) then reconfigure their architectures according to the RTL instructions of the EDA software. The FPGAs (2448 and 2450) in the therapeutic modules coordinate the therapeutic module(s) restructuring of compartments (2448-2466) to optimize the remedies.

Figure 25:
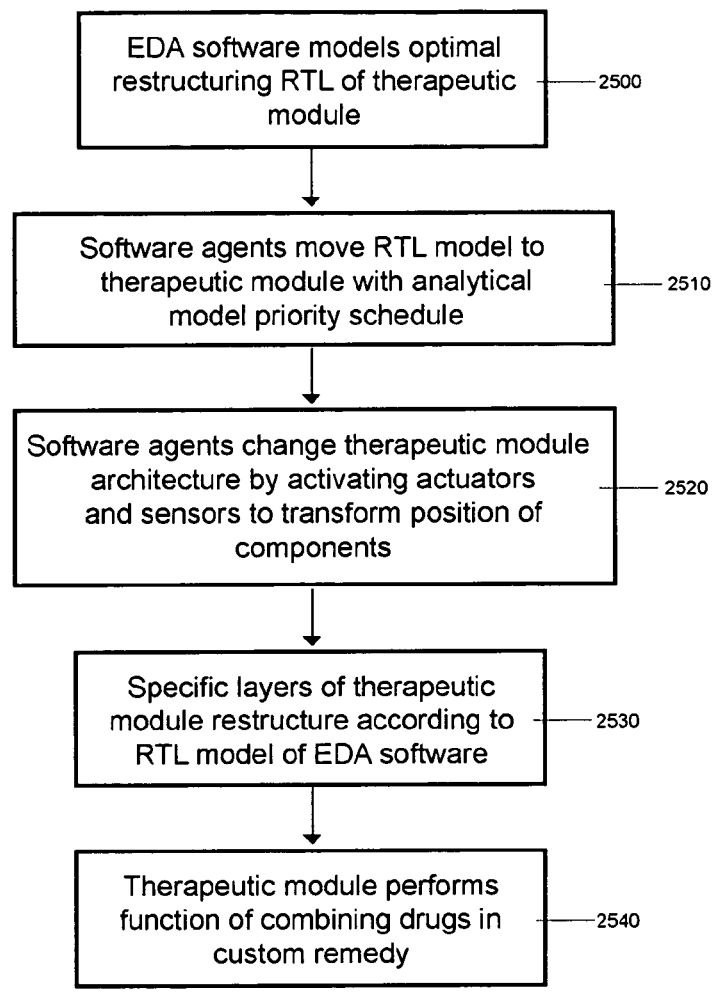
FIG. 25 is a flow chart describing the process using software agents to restructure the therapeutic module in an iMD from EDA software models.

FIG. 25 shows the process of using software agents to restructure the therapeutic module components in an iMD. EDA software initially models optimal restructuring RTL of the therapeutic module (2500) and then software agents move the RTL model to the therapeutic module with the analytical model priority schedule (2510). The software agents change therapeutic module architecture by activating actuators and sensors to transform the position of components (2520). Specific layers of the therapeutic module restructure according to the RTL model of EDA software (2530). The therapeutic module then performs a function of combining drugs in a custom remedy (2540).

Figure 26:
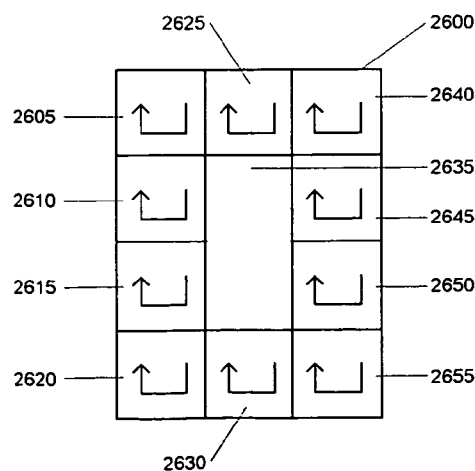
FIG. 26 is a drawing of a side view of layers of a restructuring therapeutic module in an iMD with 3D EDA modeling.

FIG. 26 shows a side view of layers of a restructuring therapeutic module in an iMD with 3D EDA modeling. Since each therapeutic module consists of multiple compartments and layers, the present invention uses 3D EDA to organize the 3D components of the therapeutic module. The three main layers of the therapeutic module are shown restructuring the compartments (2605 to 2630 and 2640 to 2655) around the central compartment (2635). This process may occur in a series of progressions so as to maintain partial functionality of the device while the restructuring occurs so as to maximize efficiency.

Figure 27:
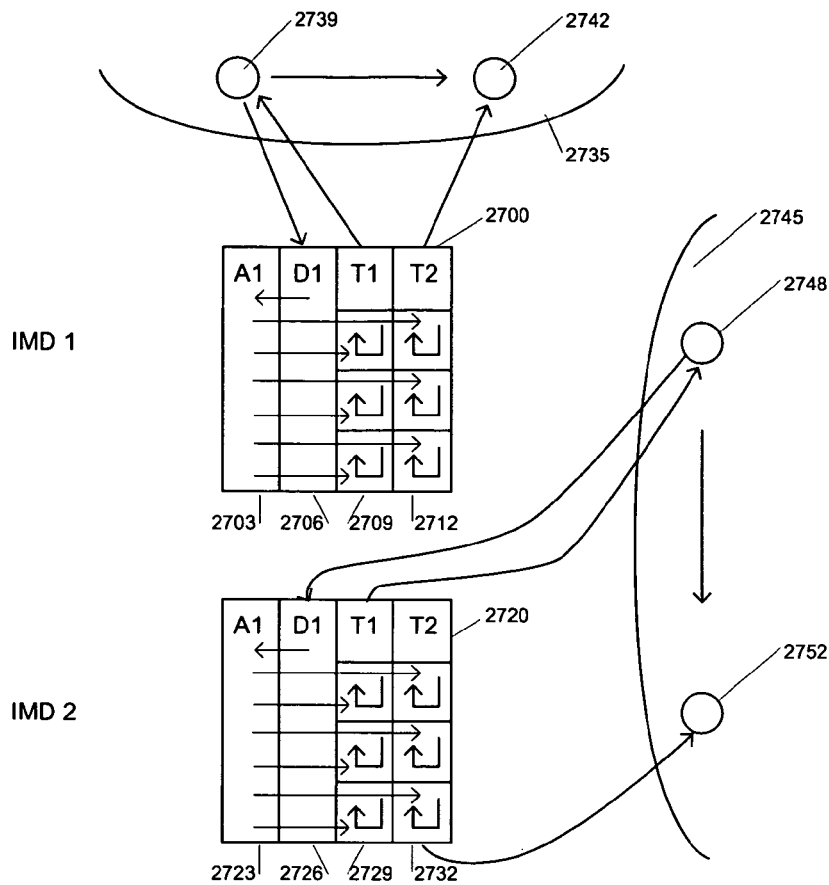
FIG. 27 is a schematic diagram showing the continuous restructuring to solve multiple evolutionary pathologies with two iMDs simultaneously.

FIG. 27 shows the continuous restructuring process to solve multiple evolutionary pathologies with two iMDs simultaneously. The diagnostic module (2706) at iMD 1 (2700) collects cell samples (2739) from a tissue (2735), analyzes the samples in the LOC and μTAS and software agents send the data to the analytical module (2703) for modeling. The software agents construct a model of the data and develop solution options that are forwarded to the therapeutic module 1 (2709). The therapeutic module 1 restructures its compartments in order to optimize the therapy, combines biologicals and chemicals to develop a novel remedy and applies the remedy at 2739. At the same time, the diagnostic module (2726) at iMD 2 (2720) collects cell samples (2748) from another tissue (2745), analyzes the samples in the LOC and μTAS and software agents send the data to the analytical module (2723) for modeling. The software agents construct a model of the data and develop solution options that are forwarded to therapeutic module 1 (2729). Therapeutic module 1 restructures its compartments in order to optimize the therapy, combines biologicals and chemicals to develop a novel remedy and applies the remedy at 2748.

However, the pathology evolves over time and the cell samples from the changed pathology are collected and analyzed by the diagnostic module 1 of iMD 2 from tissue 2735. These new samples are tested in the diagnostic module LOC and μTAS and the data transferred to the analytical module by software agents that modify the model. Updated model solution options are then forwarded by the software agents to therapeutic module 2 (2712), which restructures its compartment configuration in order to optimize the remedy, combines biologicals and chemicals and applies the revised remedy to a new cell site at 2742. This process is repeated with iMD 2 and tissue 2745 by supplying a novel remedy at 2752.

Figure 28:
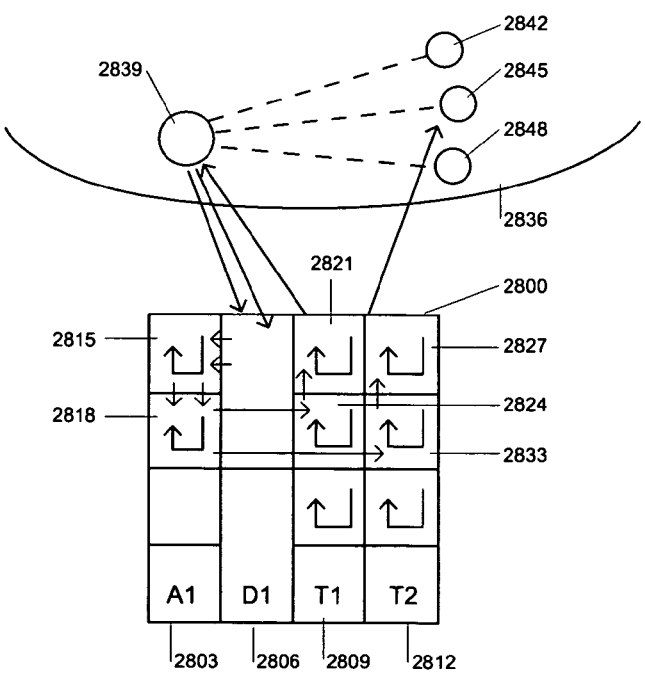
FIG. 28 is a schematic diagram showing the use of an iMD to predict disease evolutionary vectors with scenario options by anticipating architecture transformation based on disease evolution prediction scenarios.

FIG. 28 describes the use of an iMD to predict disease evolutionary vectors with scenario options by anticipating architecture transformation based on disease evolution prediction scenarios. Once cell samples are collected from the cell site at 2839 in tissue at 2836 by the diagnostic module (2806) and tested in the LOC and μTAS, software agents transfer the data to the analytical module (2803). The analytical module software agents build a model, restructure the SoC and FPGAs in order to optimize the modeling process and the model develops solution options which are transferred by software agents to therapeutic module 1 (2824 order to develop a customized solution specified by the model, therapeutic module 1 transforms its configuration by modifying the structure of its compartments, combines biologicals and chemicals into a remedy and applies the remedy to the cell site at 2839.

New cell samples are collected to assess the performance of the remedy, the LOC and μTAS analyze the samples and software agents transfer the data to the analytical module. Software agents facilitate the building of an updated model of the disease progression. The model predicts disease evolution vectors and scenarios options (2842, 2845 and 2848). The model constructs solution options based on the disease vectors and software agents forward the solution options to the therapeutic module 2 (2812). The therapeutic module 2 software agents facilitate the restructuring of the configuration of the compartments by using EDA software and, after combining the biologicals and chemicals in the model remedy, applies the remedy to the disease in new locations as they are evolved. Application of this approach involves anticipation of disease evolution vectors and then develops a reconfiguration of the therapeutic modules based on the optimal solution options to satisfy the constraints of the predicted disease evolution.

Figure 29:
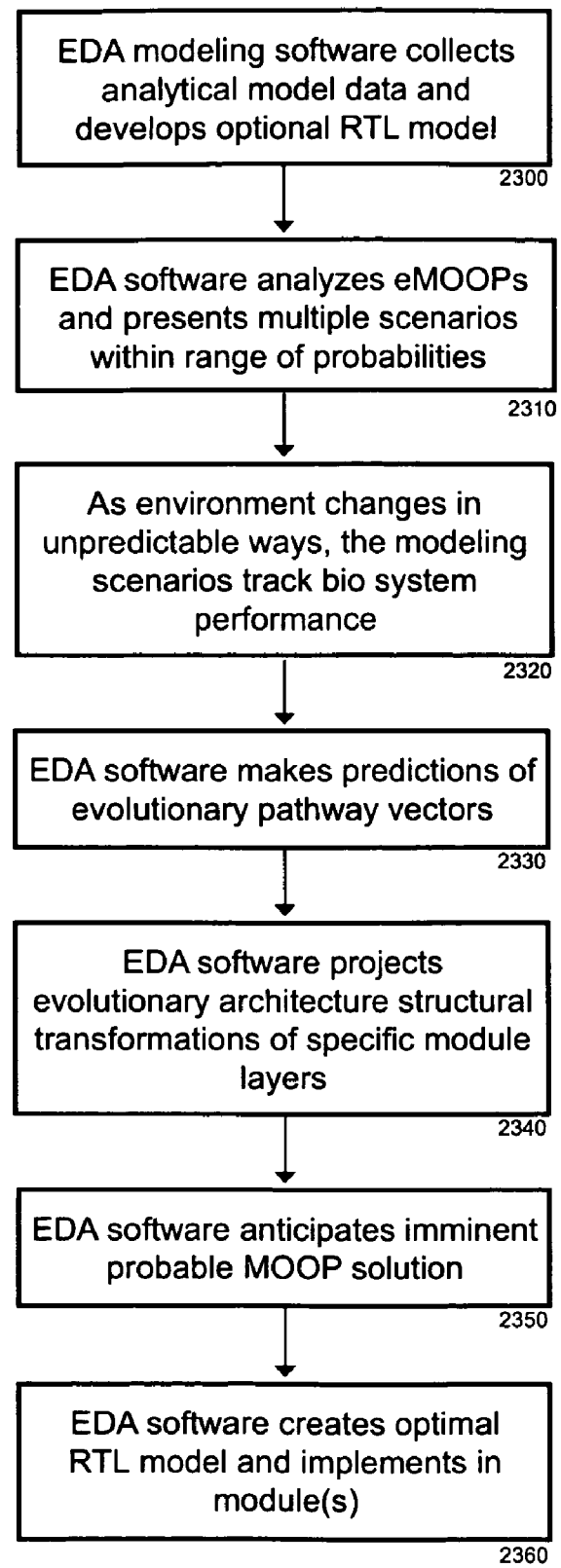
FIG. 29 is a flow chart describing the process of using EDA software to model evolutionary architecture structural transformations in an iMD.

FIG. 29 shows the process of using EDA software to model evolutionary architecture structural transformations in an iMD. After the EDA modeling software collects analytical model data and develops an optimal RTL model (2900), the EDA software analyzes evolutionary multi-objective optimization problems (eMOOPs) and presents multiple scenarios within a range of probabilities (2910). As the environment changes in unpredictable ways, the modeling scenarios track the bio system performance (2920) by obtaining input from probes collecting cell samples, and the EDA software makes predictions of evolutionary pathway vectors (2930). The EDA software projects evolutionary architecture structural transformations of specific module layers (2940) and the EDA software then anticipates an imminent probable MOOP solution (2950). The EDA software creates an optimal RTL model and implements it in the module(s) (2960).

FIG. 30 is a table of hybrid metaheuristics applied to neurological, cardiological, cancer, immunological and endocrinological systems. The main algorithm categories are local search (scatter search, tabu search and adaptive memory programming), genetic algorithms, swarm intelligence (ant colony optimization, particle swarm optimization and stochastic diffusion search) and the artificial immune system. The system also uses artificial neural network and spiking neural networks for learning. The main metaheuristic techniques are combined as shown in the table in different contexts of the investigative and therapeutic regimen involving iMD functionality. Though this is not intended to be a complete list, it captures the different strengths of the hybrid metaheuristic techniques to solve problems involving the diagnosis and treatment of disease using the iMD system. Further, the metaheuristics are useful for prediction and anticipation of conditions, particularly in evolutionary optimization problems. In general, metaheuristics apply an efficiency test to select the most efficient route of problem solving.

Figure 31:
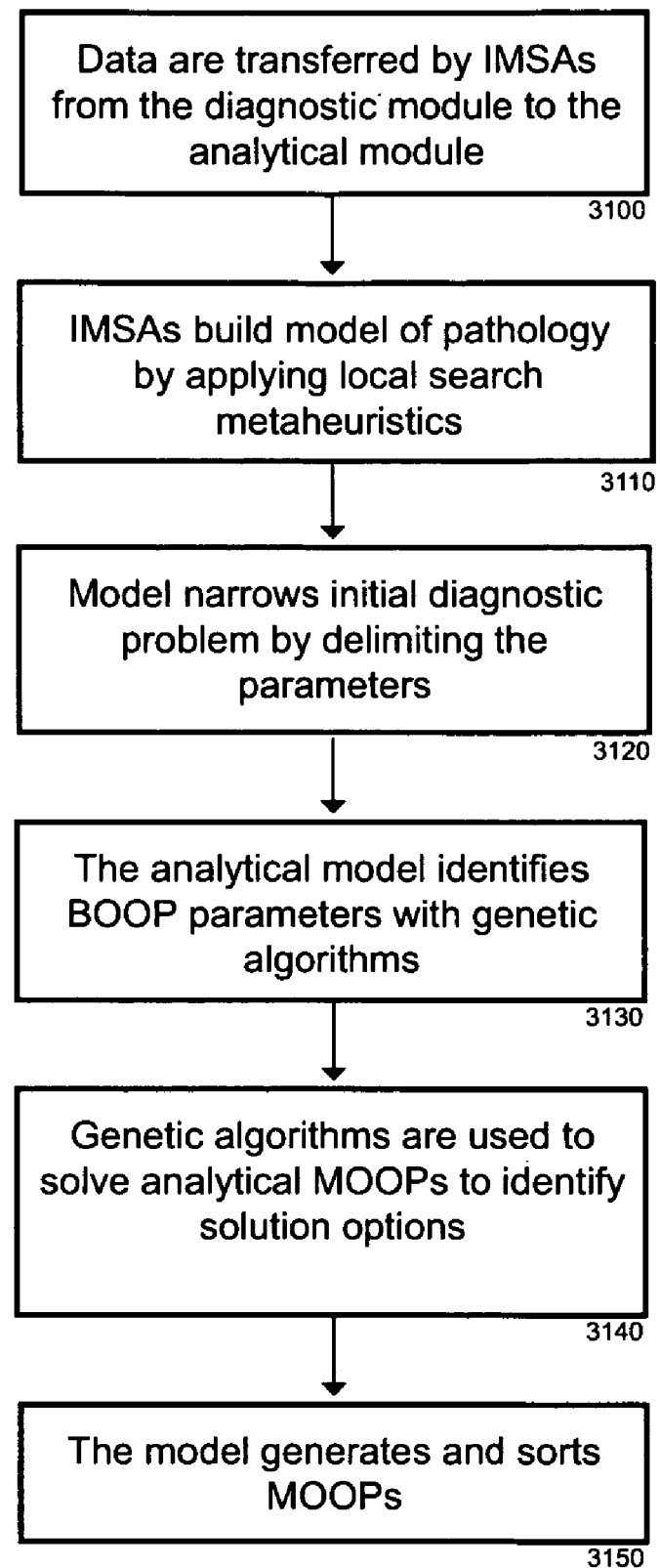
FIG. 31 is a flow chart describing the process of building and refining a model to solve optimization problems using an iMD analytical module.

FIG. 31 shows the process of building and refining a model to solve optimization problems using an iMD analytical module. Once data are transferred by software agents from the diagnostic module to the analytical module (3100), the software agents build a model of pathology by applying local search metaheuristics (3110) and the model narrows the initial diagnostic problem by delimiting the parameters (3120). The analytical model identifies bi-objective optimization problem (BOOP) parameters with genetic algorithms (3130) and the genetic algorithms are used to solve analytical MOOPs to identify solution options (3140). The model then generates and sorts multi-objective optimization solution (MOOS) options (3150).

Figure 32:
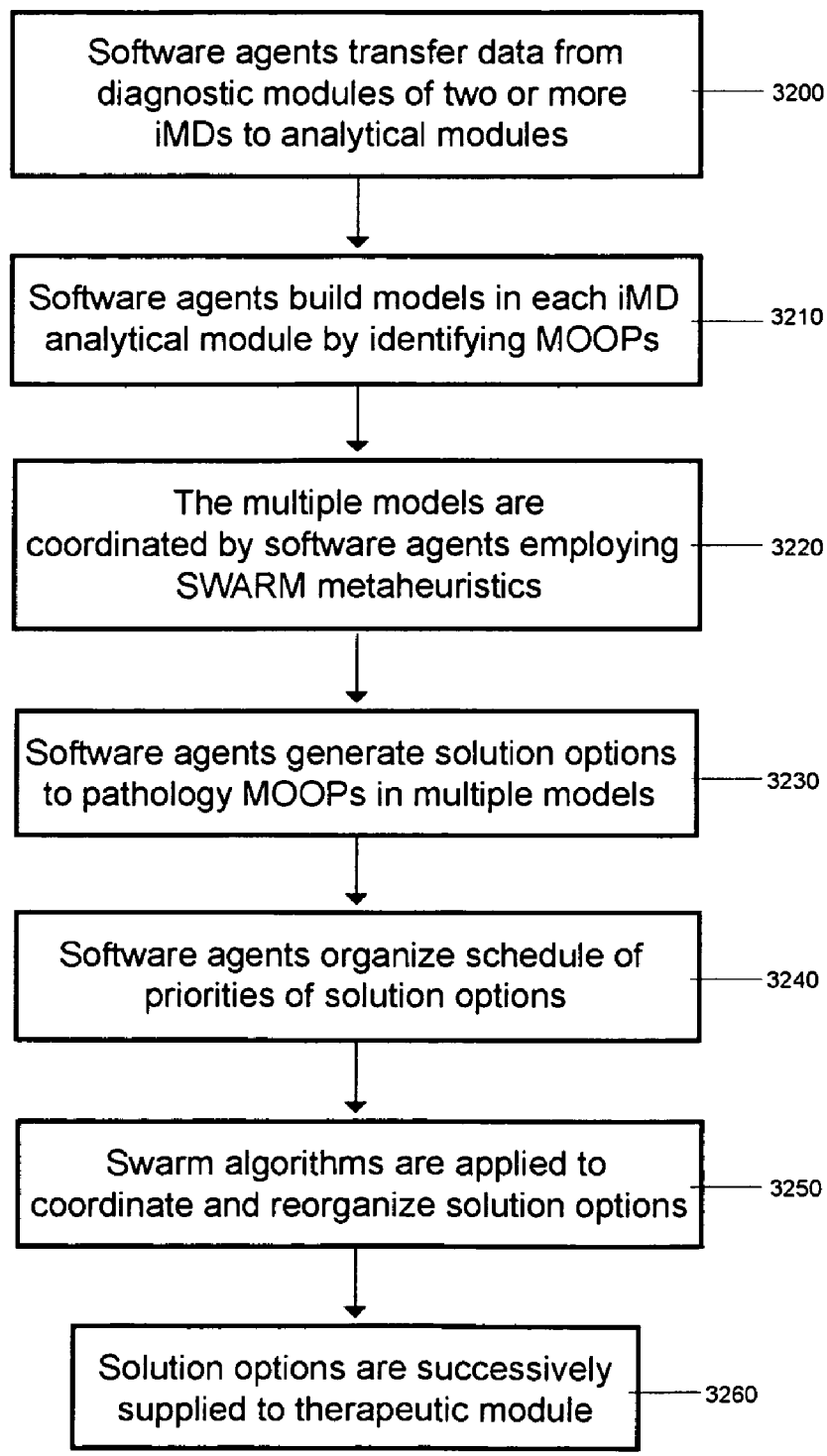
FIG. 32 is a flow chart describing the process of using swarm intelligence algorithms to solve optimization problems in the analytical module of an iMD.

FIG. 32 shows the process of using swarm intelligence algorithms to solve optimization problems in the analytical module of an iMD. After the software agents transfer data from the diagnostic modules of two or more iMDs to analytical modules (3200), the software agents build models in each iMD analytical module by identifying MOOPs (3210). The multiple models are coordinated by software agents employing swarm intelligence metaheuristics (3220). The software agents generate solution options to pathology MOOPs in multiple models (3230) and then organize a schedule of priorities of solution options (3240). Swarm algorithms are applied to coordinate and reorganize solution options (3250), which are successively supplied to the therapeutic module(s) (3260). In some cases hybrid algorithms are constructed for the modeling, scheduling and rescheduling functions that combine traveling salesman algorithms with swarm intelligence metaheuristic algorithms.

Figure 33:
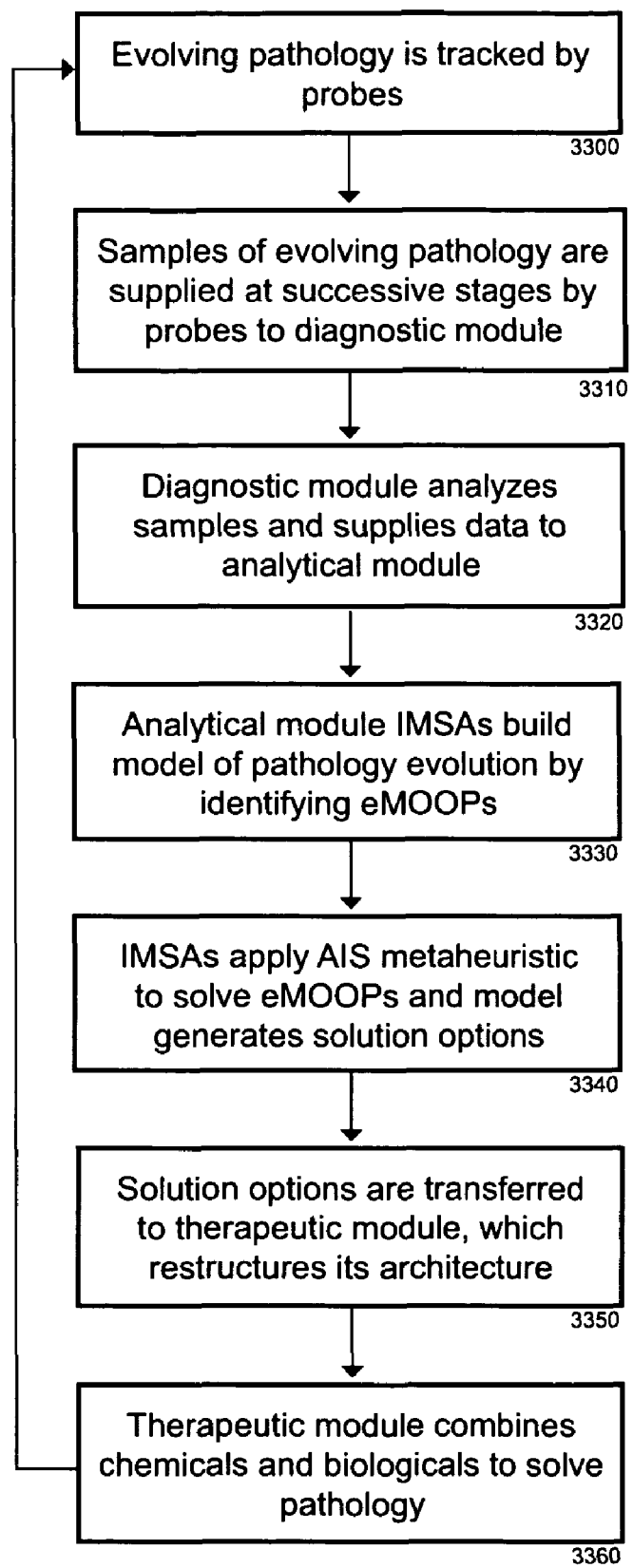
FIG. 33 is a schematic diagram showing the process of the acquisition and analysis of biological samples, the building of a model in the analytical module of an iMD using software agents and the use of immunocomputing to solve optimization problems.

FIG. 33 shows the process of the acquisition and analysis of biological samples, the building of a model in the analytical module of an iMD using software agents and the use of immunocomputing to solve optimization problems. First, the pathology is tracked by probes as it evolves (3300). The samples of the evolving pathology are supplied at successive stages by probes to the diagnostic module (3310), which analyzes samples and supplies the data to the analytical module (3320). The analytical module software agents build a model of pathology evolution by identifying eMOOPs (3330), the software agents apply the artificial immune system (AIS) metaheuristic to solve eMOOPs and the model then generates solution options (3340). The solution options are transferred to the therapeutic module(s), which restructures its architecture (3350). The therapeutic module combines chemicals and biologicals to solve pathology (3360).

Figure 34:
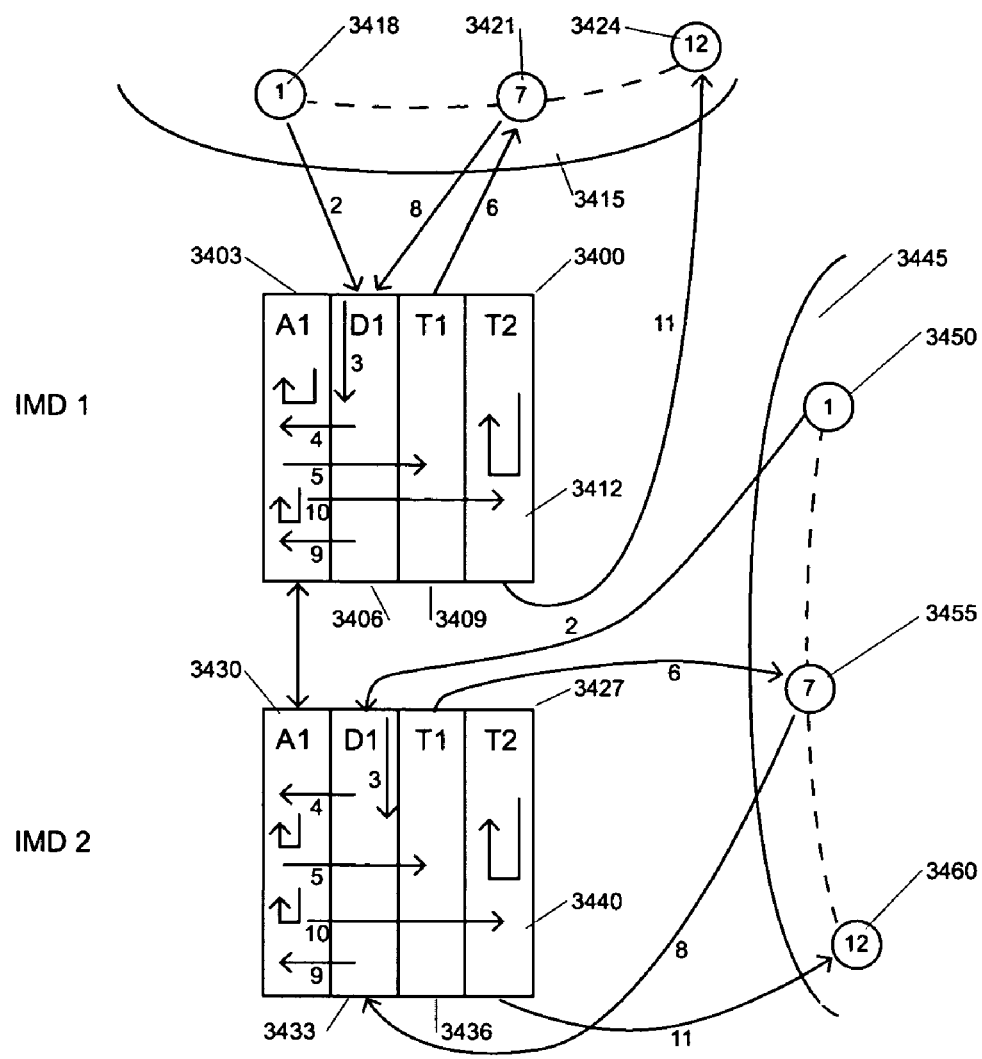
FIG. 34 is a schematic diagram showing the sequential operations of two iMDs solving problems using hybrid metaheuristics in two simultaneous pathologies.

FIG. 34 shows the sequential operations of two iMDs solving problems using hybrid metaheuristics in two simultaneous pathologies as the pathologies evolve. The drawing contains a combination of processes to solve the evolving pathologies, including pathology detection, data collection, diagnostic problem solving, scheduling, integrated circuit restructuring, therapeutic module restructuring, custom drug therapy design, delivery and assessment, pathology tracking and drug modulation, which hybrid metaheuristics apply at each stage.

In FIG. 34, pathology is detected and cell samples collected at 3418 by the diagnostic module (3406) of iMD 1 (3400). The diagnostic module LOC and µTAS test and analyze the samples and software agents forward the data to the analytical module (3403), which models the data. The SoC and FPGAs of the analytical module restructure their configurations to optimize the modeling process. Solution options for solving the evolving pathology are mapped by anticipating the scenario vectors of the pathology. The solution options are forwarded by the software agents to therapeutic module 1 (3409), which combines biologicals and chemicals into a novel remedy to solve the pathology. The pathology has evolved to position 3421, the location at which the remedy is applied.

New cell samples are collected from 3421 by the diagnostic module in order to assess the remedy. Software agents forward the data from the LOC and µTAS to the analytical module for updating the model. The semiconductors again restructure until the model is optimized and solution options are revised and forwarded by software agents to therapeutic module 2 (3412). Therapeutic module 2 reconfigures its architecture in order to optimize the formulation of a novel solution and applies the remedy to the evolved pathology at position 3424. The pathology is finally solved or managed.

This process repeats for the tissue at 3445, in which cell samples are collected at 3450 and then 3455 by iMD 2 (3427) until the pathology is solved at 3460. The two iMDs share analytical module resources, which allow them to share computer and modeling resources and therefore to share therapeutic applications for different pathologies.

Figure 35:
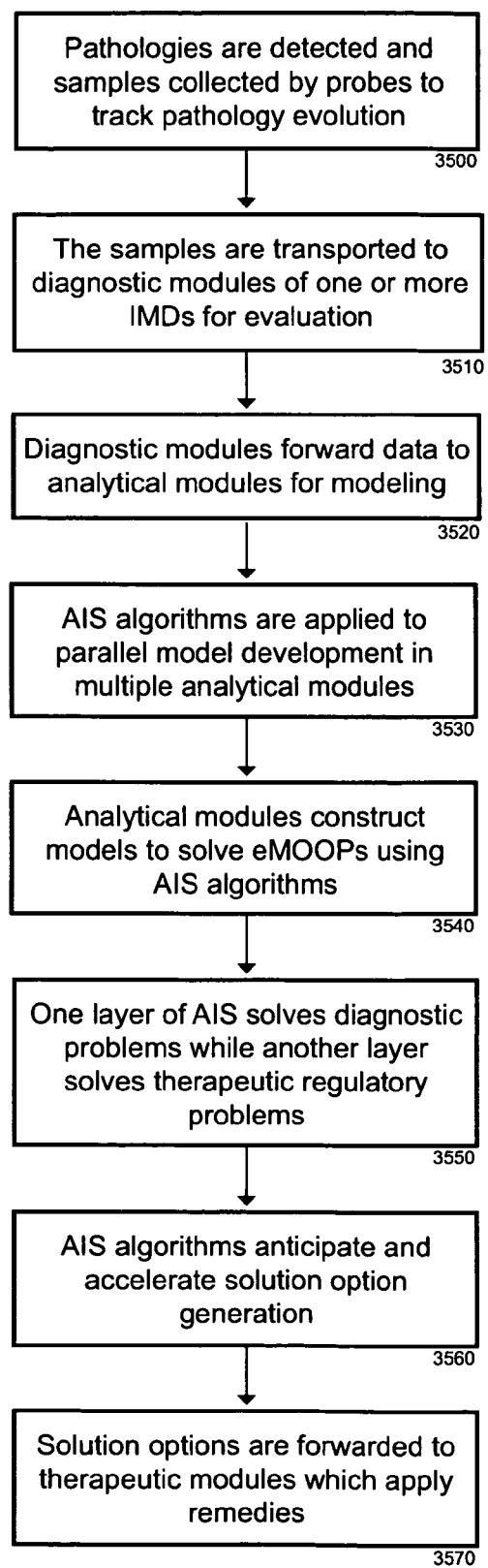
FIG. 35 is a flow chart describing the process of using immunocomputing algorithms to solve complex optimization problems in an iMD.

FIG. 35 shows the process of using immunocomputing algorithms to solve complex optimization problems in an iMD. After the pathologies are detected and samples collected by probes to track pathology evolution (3500), the samples are transported to diagnostic modules of one or more iMDs for evaluation (3510). The diagnostic modules forward data to analytical modules for modeling (3520) and AIS algorithms are applied to parallel model development in multiple analytical modules (3530). The analytical modules construct models to solve eMOOPs using AIS algorithms (3540). One layer of the AIS solves the diagnostic problems while another layer solves therapeutic regulatory problems (3550). The AIS algorithms anticipate and accelerate solution option generation (3560). Solution options are then forwarded to the therapeutic modules, which apply the remedies (3570).

Figure 36:
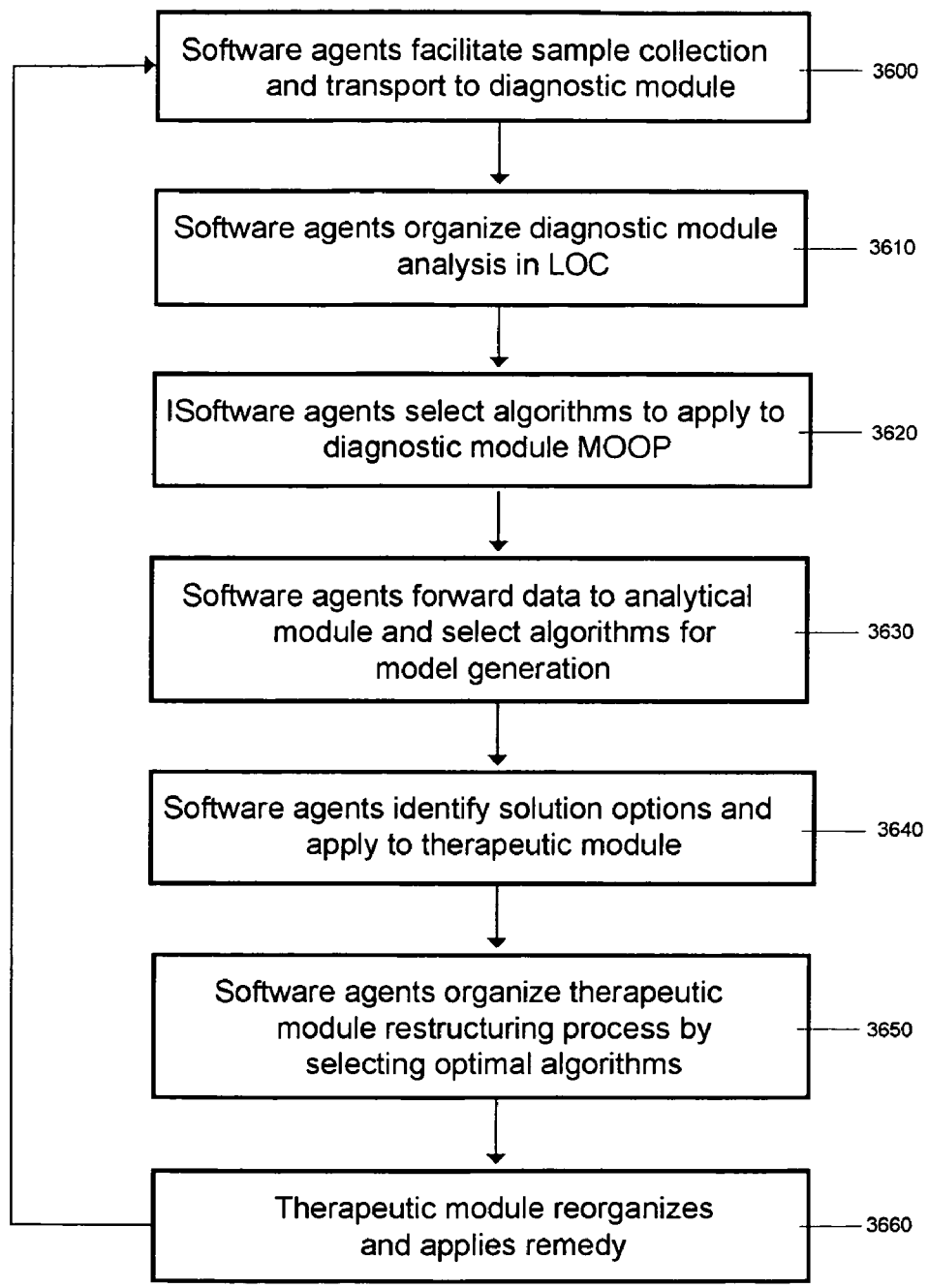
FIG. 36 is a flow chart describing the process of using software agents to diagnose and solve optimization problems in an iMD.

FIG. 36 shows the process of using software agents to diagnose and solve optimization problems in an iMD. Once software agents facilitate sample collection and transport to the diagnostic module (3600), they organize the diagnostic module analysis in the LOC (3610) and select algorithms to apply to diagnostic module MOOPs (3620). The software agents forward the data to the analytical module and select algorithms for model generation (3630). The software agents then identify solution options and apply them to the therapeutic module (3640). The software agents organize the therapeutic module structuring process by selecting optimal algorithms (3650) and the therapeutic module reorganizes and constructs and applies a remedy (3660).

Figure 37:
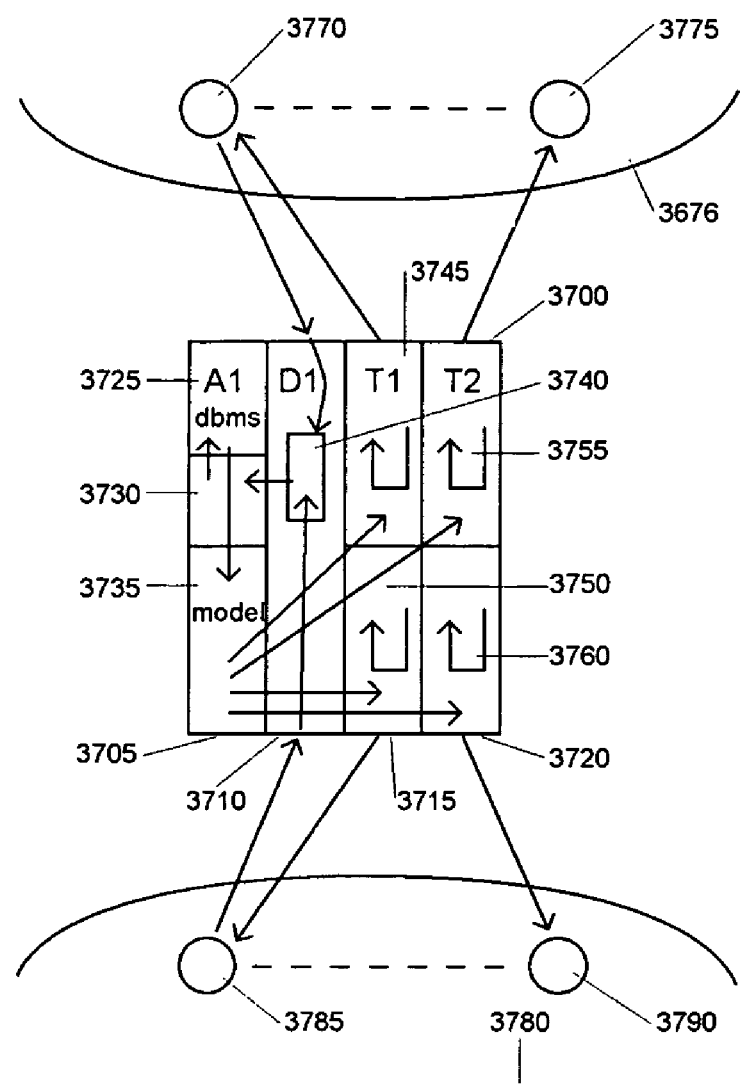
FIG. 37 is a schematic diagram showing algorithm switching at each stage of solving multiple optimization problems in an iMD.

FIG. 37 shows the algorithms switching at each stage of solving multiple optimization problems in an iMD. At each point along the chain of events of solving a problem with a pathology, a different function is performed and a different algorithm is applied. Software agents facilitate the handoff of the algorithms from point to point along the chain of the process. The cell sample collection to the diagnostic module LOC and µTAS analysis is one phase, the transfer of the data from the diagnostic module to the analytical module is another phase. The modeling process is an additional phase of the process. The transfer by software agents of the solution options from the model to therapeutic module 1 and the restructuring of the therapeutic module, the combination of the elements for a novel drug and the application of the drug to the pathology are all phases in which different algorithms are used for each function by the software agents. This process repeats until the pathology is solved or managed in the two tissues (3765 and 3780) shown, as the pathologies evolve, which the iMD simultaneously treats.

Figure 38:
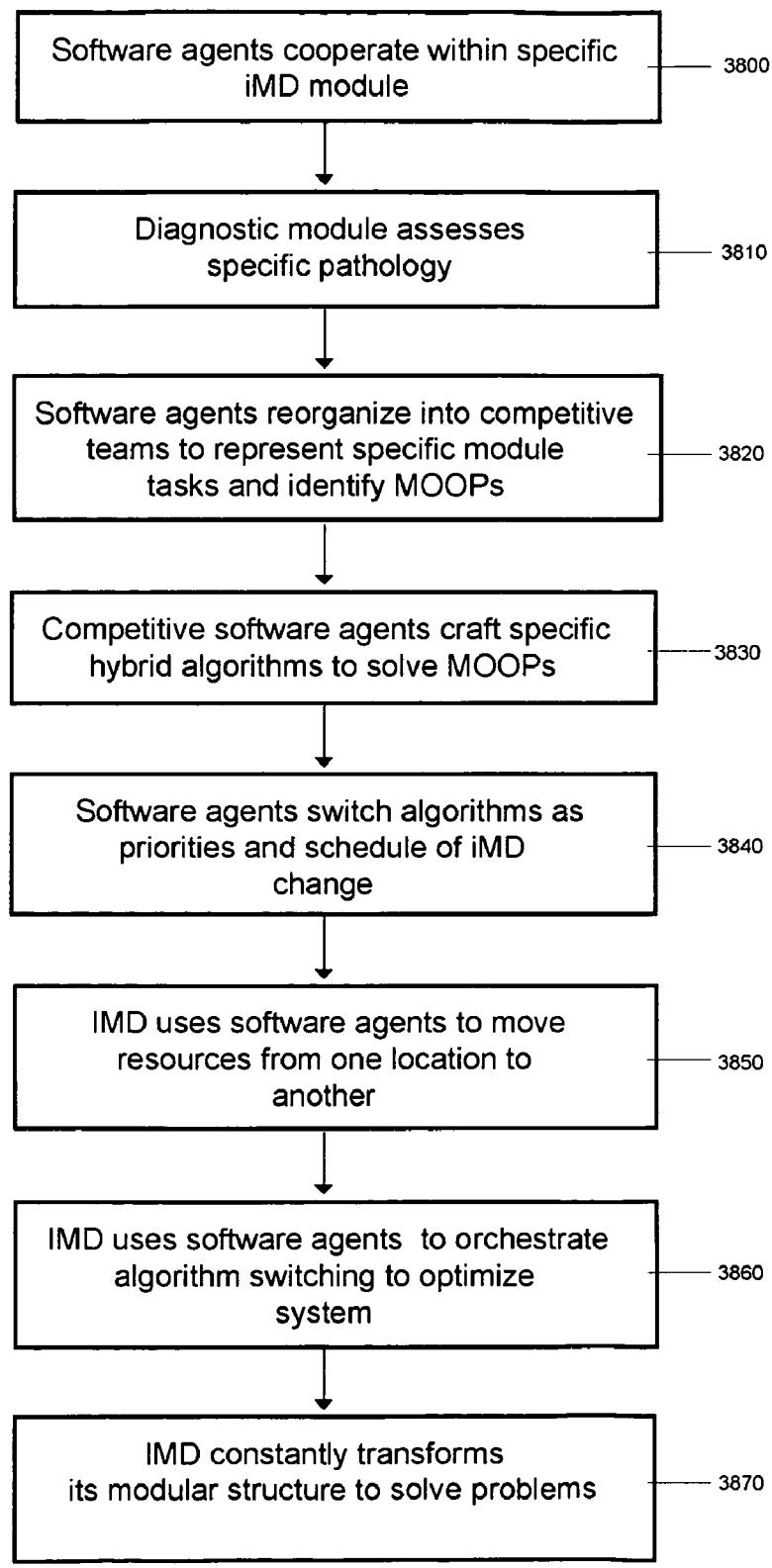
FIG. 38 is a flow chart describing the process of using software agents to switch algorithms to solve optimization problems in an iMD.

FIG. 38 shows the process of using software agents to switch algorithms to solve optimization problems in an iMD. After the software agents cooperate within a specific iMD module (3800), the diagnostic module assesses a specific pathology (3810) and the software agents reorganize into competitive teams to represent specific module tasks and identify MOOPs (3820). The competitive software agents craft specific hybrid algorithms to solve MOOPs (3830) and the software agents switch algorithms as priorities and the schedule of the iMD change (3840). The iMD uses software agents to move resources from one location to another (3850) and the software agents orchestrate algorithm switching to optimize the system (3860). The iMD constantly transforms its modular structure to solve problems (3870).

I claim:

1. A system for operation of a medical device for therapeutics, comprising:
   a therapeutic module consisting of at least two layers;
   an analytical module consisting of a system-on-a-chip (SoC) and sensors;
   a set of compartments for the storage and combination of chemicals and biologicals;
   a set of electrical interconnects;

a set of microfluidic components, including tubes, valves, actuators and gates;
at least one integrated circuit;
wherein device components are connected by the electrical interconnects;
wherein the computation operations of the medical device are controlled by an integrated circuit;
wherein when biological specimens are input into the analytical module, the analytical module analyzes the specimens;
wherein the analytical module uses the SoC to model solutions to pathology optimization problems;
wherein the analytical module transfers model solution data to the therapeutic module on a specific combination of chemicals and biologicals to remedy a patient pathology;
wherein the medical device components include a set of compartments for combining chemicals and biologicals on at least one of a set of layers;
wherein the medical device coordinates the transfer of chemicals and biologicals by using an integrated circuit to control the microfluidic components to distribute the chemicals and biologicals in specific measured doses according to the model recommendations from specific compartments in the medical device to a common compartment;
wherein the chemicals and biologicals are combined in a common compartment of the medical device on one of a set of layers; and
wherein the selected combination of chemicals and biologicals is transferred from the therapeutic module of the medical device to a cell site in a patient.

2. A medical device apparatus for generating customized medicines, comprising:
a therapeutic module consisting of at least two layers;
an analytical module consisting of a system-on-a-chip (SoC) and sensors;
a set of compartments for the storage and combination of chemicals and biologicals;
a set of electrical interconnects;
a set of microfluidic components, including tubes, valves, actuators and gates;
at least one integrated circuit;
wherein the layers of components are connected by the electrical interconnects;
wherein the computation operations of the medical device are controlled by an integrated circuit;
wherein when biological specimens are input into the analytical module, the analytical module analyzes the specimens;
wherein the analytical module uses the SoC to model solutions to pathology optimization problems;
wherein the SoC in the analytical module transfers data on the solution options from the model to the therapeutic module;
wherein the medical device components include a set of compartments for combining chemicals and biologicals on at least one of a set of layers;
wherein the medical device microfluidic components are coordinated to release specific chemicals and biologicals on at least one of a set of layers;
wherein the medical device is organized to route chemicals and biologicals from storage compartments into a common compartment of the device;
wherein the medical device uses the microfluidic components to coordinate the at least one chemical or biological in specific measured doses according to the model recommendations;
wherein the at least one chemical or biological is transferred to a common compartment of the medical device module in one of a set of layers;
wherein the resulting at least one chemical or biological is transmitted to a cell site in a patient; and
wherein the therapeutic remedy that consists of the application of the at least one chemical and biological is assessed by sensors connected to the device's analytical module.

3. The system of claim 1:
wherein the medical device stores specific chemicals and biologicals in chambers accessible to the therapeutic module by microfluidic components.

4. The system of claim 1:
wherein the medical device compartments are organized to transform their configurations; and
wherein the medical device components on one layer transform their configuration by folding gates down to remove partitions and folding gates up to add partitions to create newly configured compartments.

5. The system of claim 4:
wherein the medical device flushes fluids from its compartments before the transformation process is initiated.

6. The system of claim 4:
wherein feedback data are obtained about the remedy used by the therapeutic module;
wherein the analytical module uses feedback data to update the model;
wherein the updated solution options on the pathology are sent to the therapeutic module;
wherein the therapeutic module reconfigures configuration options to solve the pathology;
wherein the therapeutic module combines a new set of chemicals and biologicals according to the revised model in a chamber on one of its layers; and
wherein the resulting revised therapeutic combination of chemicals and biologicals is transmitted to a cell site in a patient.

7. The system of claim 6:
wherein the process of analysis and therapy continues until the pathology is controlled.

8. The apparatus of claim 2:
wherein the SoC uses hybrid metaheuristics to solve the optimization problems.

9. The apparatus of claim 2:
wherein the medical device compartments are capable of transforming their configurations; and
wherein the medical device components on one layer transform their configuration by folding gates down to remove partitions and folding gates up to add partitions to create newly configured compartments.

10. The apparatus of claim 1:
wherein the pathology addressed is evolutionary; and
wherein the SoC of the analytical module continuously operates to satisfy the constraints of solving the evolutionary optimization problem presented by the evolving pathology.

11. The apparatus of claim 1:
wherein feedback data are obtained about the remedy by accessing sensors connected to the analytical module;
wherein the SoC in the analytical module uses the updated data to update the model;

wherein the SoC uses configurable logic circuits to transform its structure to solve the evolving optimization problem with the most recent data;
wherein the SoC sends updated solution options about the pathology and the most recent therapy to the therapeutic module;
wherein the therapeutic module combines a new set of chemicals and biologicals according to the revised model in a chamber on one of the device's layers; and
wherein the resulting revised therapeutic combination is transmitted to a cell site in a patient.

12. The apparatus of claim 11:
wherein the therapeutic module architecture is reconfigured to optimize the combination of chemicals and biologicals.

13. The apparatus of claim 11:
wherein the process of analysis and therapy continues until the pathology is controlled.

14. The apparatus of claim 1:
wherein the SoC in the analytical module reconfigures its structure by using reconfigurable logic components in order to optimize the modeling of the pathology to select solution options.

15. A method for synthesizing customized medicines in a medical device, comprising:
a therapeutic module consisting of at least two layers;
an analytical module consisting of a system-on-a-chip (SoC) and sensors;
a set of compartments for storage of chemicals and biologicals;
a set of electrical interconnects;
a set of microfluidic components, including tubes, valves, actuators and gates;
at least one integrated circuit;
wherein the process consists of:
connecting device components with the electrical interconnects;
controlling the computation operations of the medical device with the integrated circuit;
analyzing biological specimens in the analytical module when the biological specimens are input into the analytical module;
utilizing the SoC in the analytical module to model solutions to pathology optimization problems;
transferring model solution data from the analytical module to the therapeutic module on a specific combination of chemicals and biologicals to remedy a patient pathology;
combining chemicals and biologicals on at least one of a set of layers in the medical device by using a set of compartments;
coordinating the transfer of chemicals and biologicals by using the integrated circuit to control the microfluidic components to distribute the chemicals and biologicals in specific measured doses according to the model recommendations from specific compartments in the medical device to a common compartment;
combining the chemicals and biologicals in a common compartment of the medical device on one of a set of layers; and
transferring a selected combination of chemicals and biologicals from the therapeutic module of the medical device to a cell site in a patient.

16. The method of claim 15:
wherein the method further consists of transforming the medical device compartments; and
transforming the configuration of medical device components on one layer by folding gates down to remove partitions and folding gates up to add partitions to create newly configured compartments.

17. The method of claim 15:
wherein the method further consists of reconfiguring the therapeutic module architecture to optimize the combination of chemicals and biologicals.

18. The method of claim 15:
wherein the method further consists of receiving feedback data about the remedy used by the therapeutic module;
updating the model in the analytical module by using the feedback data;
sending updated solution options on the pathology to the therapeutic module;
reconfiguring the therapeutic module configuration options to solve the pathology;
combining a new set of chemicals and biologicals in the therapeutic module according to the revised model in a chamber on one of the device's layers; and
transmitting the resulting revised therapeutic combination of chemicals and biologicals to a cell site in a patient.

19. The method of claim 15:
wherein the method further consists of obtaining feedback data about the remedy by accessing sensors connected to the analytical module;
using the SoC to update the model generated in the analytical module by using updated data;
transforming the SoC structure by utilizing configurable logic circuits to solve the evolving optimization problem with the most recent data;
sending updated solution options about the pathology and the most recent therapy generated by the SoC to the therapeutic module;
combining a new set of chemicals and biologicals according to the revised model in a chamber of the therapeutic module; and
transmitting the resulting revised therapeutic combination to a cell site in a patient.

20. The system of claim 2:
wherein at least two chemicals or biologicals are transferred to at least one cell site in a patient in a sequence of actions.

* * * * *